United States Patent
Oh et al.

(10) Patent No.: US 10,684,273 B2
(45) Date of Patent: Jun. 16, 2020

(54) USE OF PHOSPHATIDYLINOSITOL PHOSPHATE-BINDING MATERIAL FOR APOPTOSIS DETECTION

(71) Applicants: GIL MEDICAL CENTER, Incheon (KR); GACHON UNIVERSITY OF INDUSTRY-ACADEMIC COOPERATION FOUNDATION, Gyeonggi-do (KR)

(72) Inventors: Byung Chul Oh, Incheon (KR); Ok Hee Kim, Incheon (KR); Cheol Soon Lee, Incheon (KR)

(73) Assignees: GIL MEDICAL CENTER, Incheon (KR); GACHON UNIVERSITY OF INDUSTRY-ACADEMIC COOPERATION FOUNDATION, Gyeonggi-do (KR)

(*) Notice: Subject to any disclaimer, the term of this patent is extended or adjusted under 35 U.S.C. 154(b) by 0 days.

(21) Appl. No.: 15/359,140

(22) Filed: Nov. 22, 2016

(65) Prior Publication Data

US 2017/0199174 A1    Jul. 13, 2017

Related U.S. Application Data

(63) Continuation of application No. PCT/KR2016/000673, filed on Jan. 21, 2016.

(30) Foreign Application Priority Data

Jan. 21, 2015 (KR) .......................... 10-2015-0010192

(51) Int. Cl.
    *G01N 33/52* (2006.01)
    *G01N 33/53* (2006.01)
    *G01N 30/00* (2006.01)
    *G01N 33/50* (2006.01)

(52) U.S. Cl.
    CPC ....... *G01N 33/5011* (2013.01); *G01N 33/502* (2013.01); *G01N 2405/06* (2013.01); *G01N 2510/00* (2013.01)

(58) Field of Classification Search
    None
    See application file for complete search history.

(56) References Cited

U.S. PATENT DOCUMENTS

2010/0092456 A1* 4/2010 Bisset ............... C12Q 1/48
                                                424/130.1
2013/0302827 A1   11/2013 Langen

FOREIGN PATENT DOCUMENTS

| JP | 2002517188 | 6/2002 |
| JP | 2013163673 | 8/2013 |
| WO | 2009107971 | 9/2009 |

OTHER PUBLICATIONS

Prestwich, G.D., Phosphoinositide signaling: from affinity probes to pharmaceutical targets, Chem. Biol. 11:619-637. (Year: 2004).*

(Continued)

*Primary Examiner* — Claire Kaufman
(74) *Attorney, Agent, or Firm* — Hovey Williams LLP

(57) ABSTRACT

The present invention relates to a method for detecting apoptosis using a phosphatidylinositol phosphate-binding material, a method for screening anticancer agents, a method for screening apoptosis-inhibiting materials, and a method for inhibiting phagocytosis.

4 Claims, 28 Drawing Sheets

Specification includes a Sequence Listing.

(56) References Cited

OTHER PUBLICATIONS

Byekova et al., Localizastion of phosphatidulininositol (3,4,5)-triphosphate to phagosomes in Entamboeba histolytica achieved using glutathione S-trasnferase- and green fluorescent protein-tagged lipd biosensors, Infect,. Immun. (78(1):125-137, Jan. 2010.*
Jack et al., Both membrane-bound and soluble forms of CD14 bind to Gram-negative bacteria, Eur. J. Immunol. 25(5)1436-1441, 1995.*
Dillon et al., Annexin V binds to viable B cells and colocalizes with a marker of lipid rafts upon B cell receptor activation, J. Immunol. 164:1322-1332, 2000.*
T.E. Creighton, Proteins: Structures and molecular principles, (W.H. Freeman & Co.:New York), pp. 223-227,1984.*
Blankenberg et al., In vivo detection and imaging of phophatidylserine expression during programmed cell death, Proc. Natl. Acad. Sci., USA, 95:6349-6354, May 1998.*
UniProt Database, Accession No. P08758, ANXA5_Human, Dec. 5, 2018, version 212, Retrieved online from: <URL:https://www.uniprot.org/uniprot/P08758.txt>. Retrieved on Jan. 7, 2019.*
Kohout et al., C2 domains of protein kinase C isoforms alpha, beta, and gamma: activation parameteres and calcium stoichiometries of the membrane-bound state, Biochem. 41(38):11411-11424, Aug. 2002.*
Tait al., Phospholipid binding of annexin V: Effects of calcium and membrane phosphatidylserine content, Archives of Biochemi. Biophys. ,298(1):187-191, Oct. 1992.*
Smith et al. Transmembrane voltage regulates binding of annexin V and lactadherin to cells with exposed phosphatidylserine, BMC Biochem., 10:5, Feb. 17, 2009.*
Jeppersen et al., Entropic and enthalpic contributions to annexin V-membrane binding, J. Biol. Chem. 283:6126-6135, 2008.*
Chen et al., A monoclonal antibody to visulalize PtdIns(3,4,5)P3 in cells,J. Histochem. Cytochem. 50(5):697-708, 2002.*
GenBank Database, Accession No. CAP70058.1, CD14 antigen [Gallus gallus], accessed on Aug. 8, 2019, Oct. 29, 2008.*
Akashi, et al., "Regulatory Roles for CD14 and Phosphatidylinositol in the Signaling via Toll-like Receptor 4-MD-2", Biochemical and Biophysical Research Communications, 2000, vol. 268, pp. 172-177.
Corbalan-Garcia, et al., "A New Phosphatidylinositol 4,5-Bisphosphate-binding Site Located in the C2 Domain of Protein Kinase C*", 2003, J. Biol Chem., vol. 278, pp. 4972-4980.
Blunt, et al., "Pharmacological targeting of phosphoinositide lipid kinases and phosphatases in the immune system: success, disappointment, and new opportunities", Aug. 2, 2012, Frontiers in Immunology, vol. 3, Article 226, 15 pages.

Nakagawa, et al., "Caspase-activated phosphoinositide binding by CNT-1 promotes apoptosis by inhibiting the AKT pathway," Nature Structural & Molecular Biology, vol. 21, issue 12, Dec. 2014, pp. 1082-1092.
Miao, et al., "Targeting phospshatidylinositol 3-kinase signaling with novel phosphatidylinositol 3,4,5-triphosphate antagonists," Autophagy,vol. 7, issue 6, Jun. 2011, 3 pages.
Mejillano,et al., "Regulation of Apoptosis by Phosphatidylinositol 4,5-Bisphosphate Inhibition of Caspases, and Caspase Inactivation of Phosphatidylinositol Phosphate 5-Kinases," Journal of Biological Chemistry, vol. 276, issue 3, Jan. 2001, pp. 1865-1872.
Zhu, et al., "Deactivation of phosphatidylinositol 3,4,5-trisphosphate/ Akt signaling mediates neutrophil spontaneous death," PNAS, vol. 103, issue 40, Oct. 3, 2006, pp. 14836-14841.
Trahtemberg, et al., "Calcium, leukocyte cell death and the use of annexin V: fatal encounters," Apoptosis, vol. 12, 2007, pp. 1769-1780.
Schlegel, et al., "Phosphatidylserine, a death knell," Cell Death and Differentiation, vol. 8, 2001, pp. 551-563.
Fadok, et al., "Exposure of Phosphatidylserine on the Surface of Apoptotic Lymphocytes Triggers Specific Recognition and Removal by Macrophages," Journal of Immunology, vol. 148, Issue 7, Apr. 1, 1992; pp. 2207-2216.
Park, "Peptide/Gene Therapy for the Prevention of Diabetes," Hanyang Med. Rev., vol. 29, issue 2, 2009, 3 pages, abstract.
Kim, et al, "Current Strategies for Successful Islet Xenotransplantation," J. Korean Soc. Transplant, vol. 23, issue 3, Dec. 2009, 2 pages, abstract.
Shapiro, et al., "International Trial of the Edmonton Protocol for Islet Transplantation," N. Eng. J. Med., vol. 355, Issue 13, Sep. 28, 2006, pp. 1318-1330.
Cantley, "The Phosphoinositide 3-Kinase Pathway," SCIENCE, vol. 296, May 31, 2002, 5 pages.
Balla, "Inositol-lipid binding motifs: signal integrators through protein-lipid and protein-protein interactions," J. Cell Science, vol. 118, issue 10, Mar. 16, 2005, pp. 2093-2104.
Miao, et al., "Small molecule inhibition of phosphatidylinositol-3,4,5-triphosphate (PIP3) binding to pleckstrin homology domains," PNAS, vol. 107, issue 46, Nov. 16, 2010, pp. 20126-20131.
Toda, et al."Two-Step Engulfment of Apoptotic Cells," Molecular and Cellular Biology, vol. 32, issue 1, Jan. 2012, pp. 118-125.
Kim, et al.,"Crystal Structure of CD14 and Its Implications for Lipopolysaccharide Signaling," J. Bio. Chem., vol. 280, issue 12, Mar. 25, 2005, pp. 11347-11351.
Farah, et al., "The Role of C2 Domains in PKC Signaling," Calcium Signaling, 2012, pp. 663-683.
International Search Report for related Korean PCT Application No. PCT/KR2015/000673, dated May 25, 2016 (English translation attached).

* cited by examiner

[Fig. 1a]
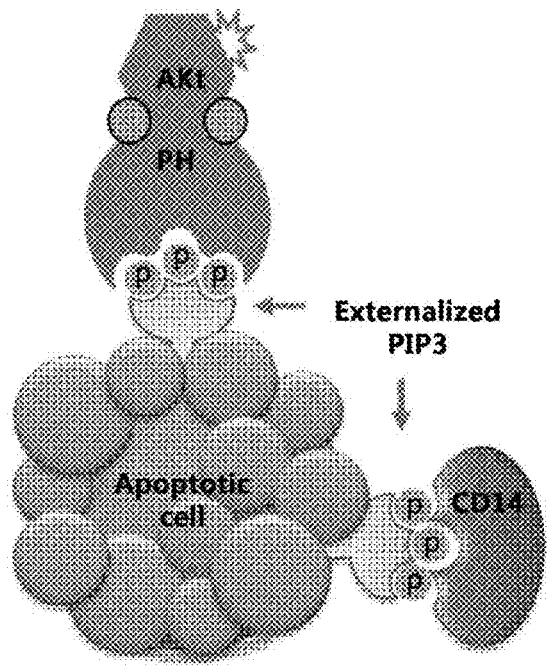
[Fig. 1b]
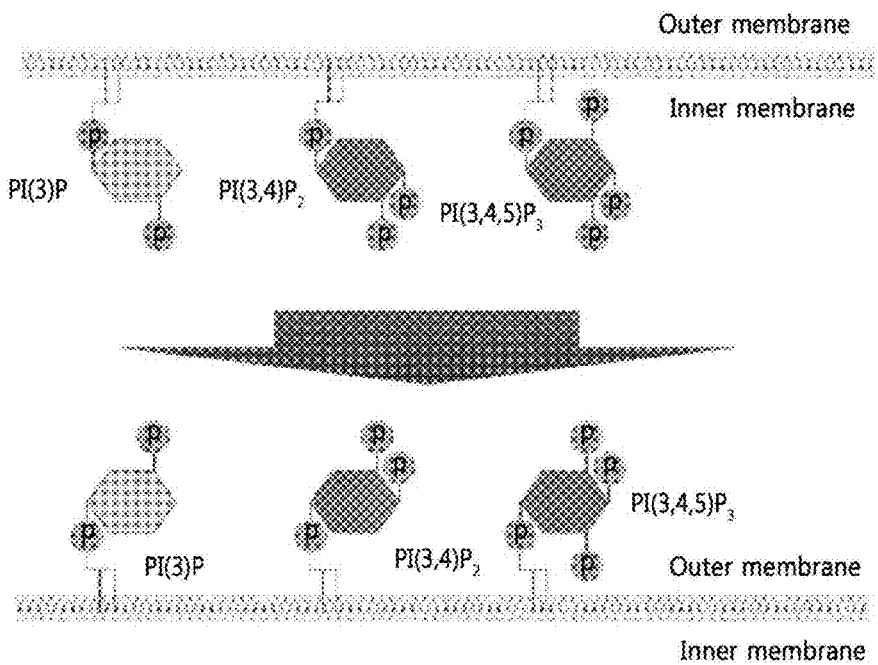

[Fig. 1c]
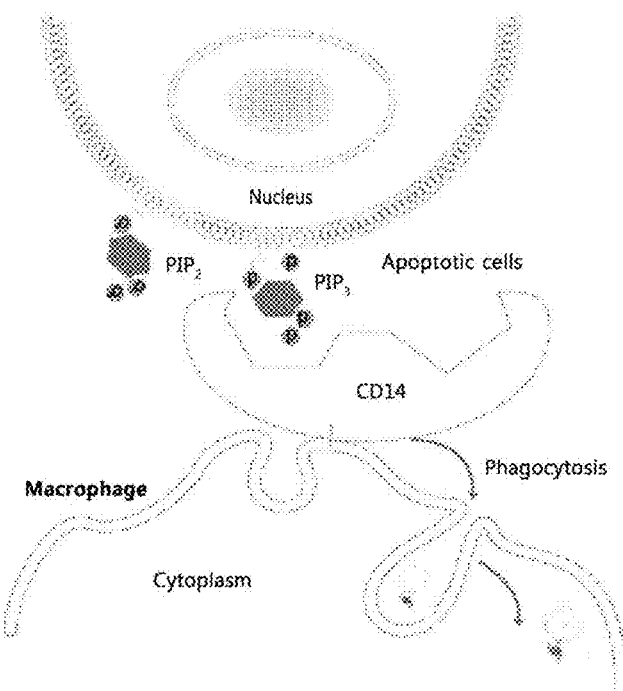

[Fig. 2a]
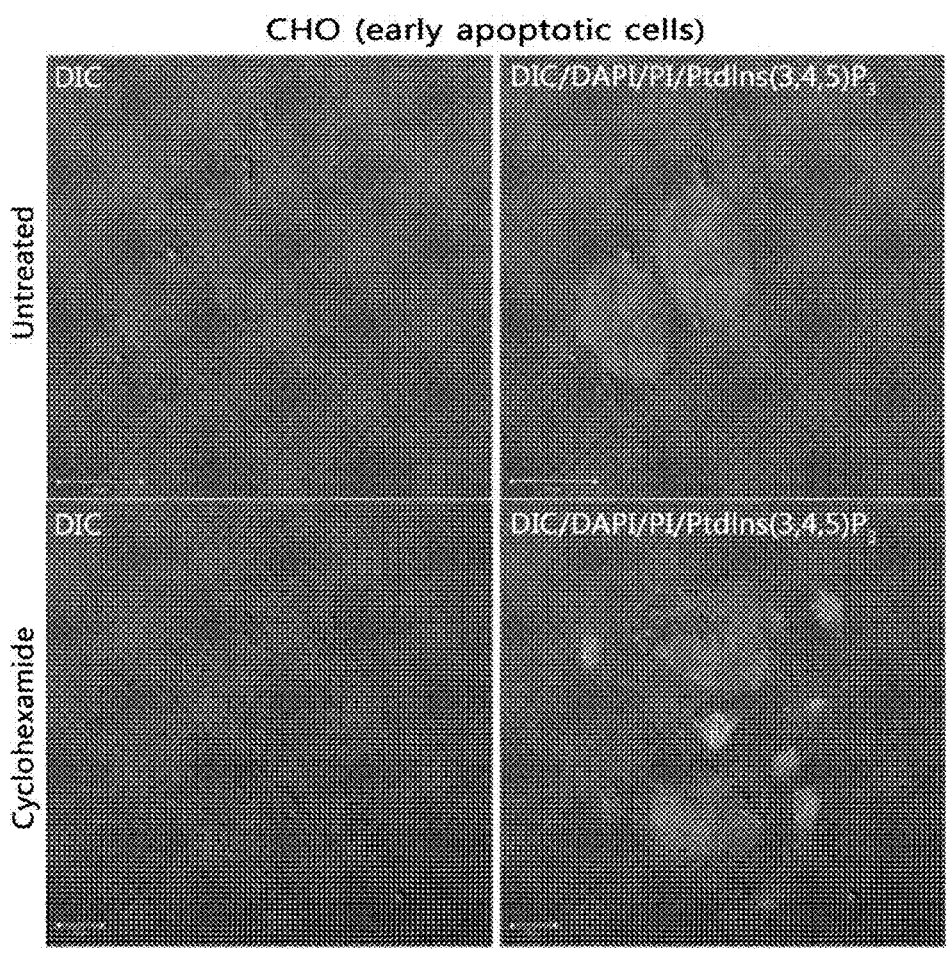

[Fig. 2b]
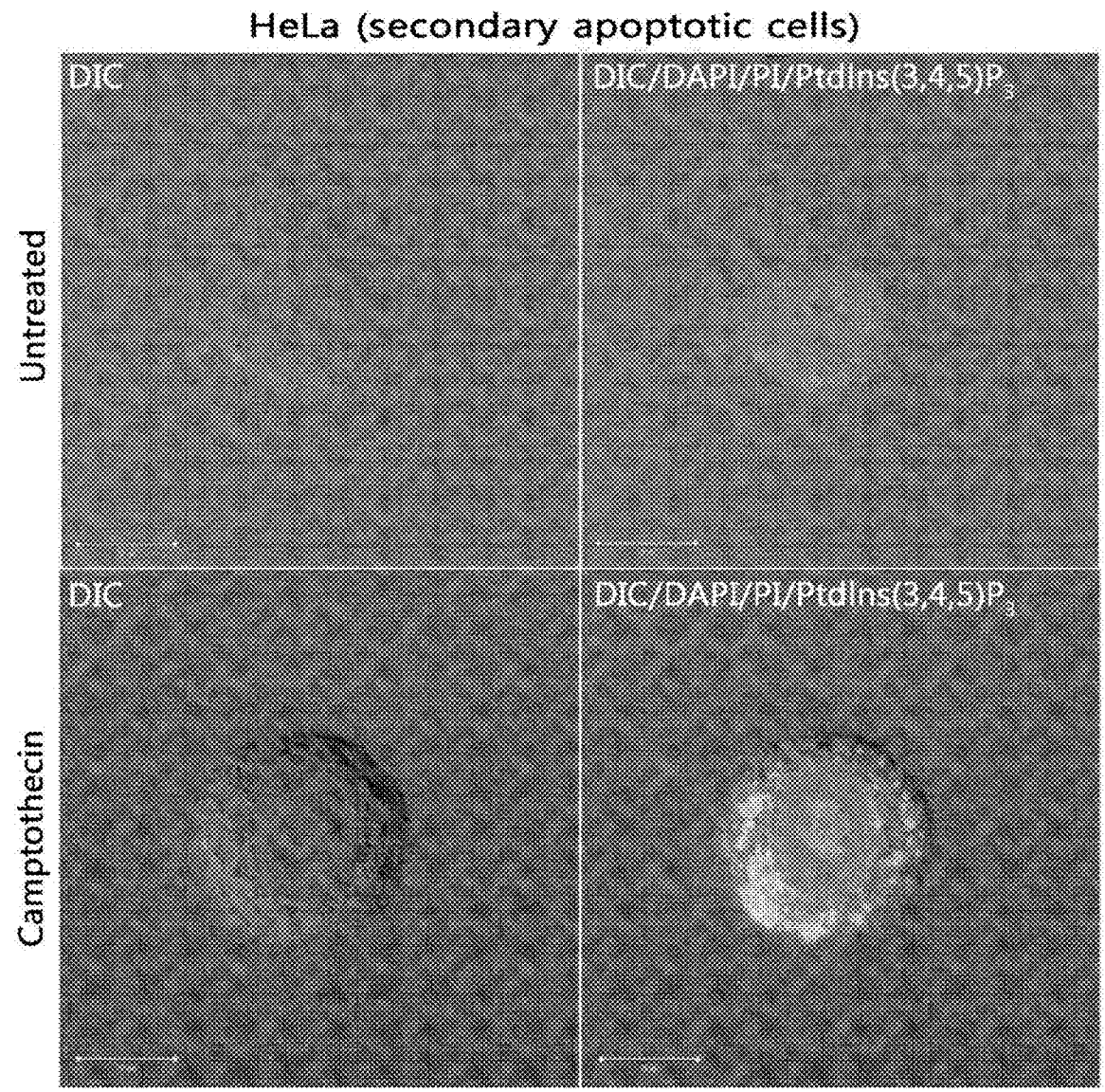

[Fig. 2c]
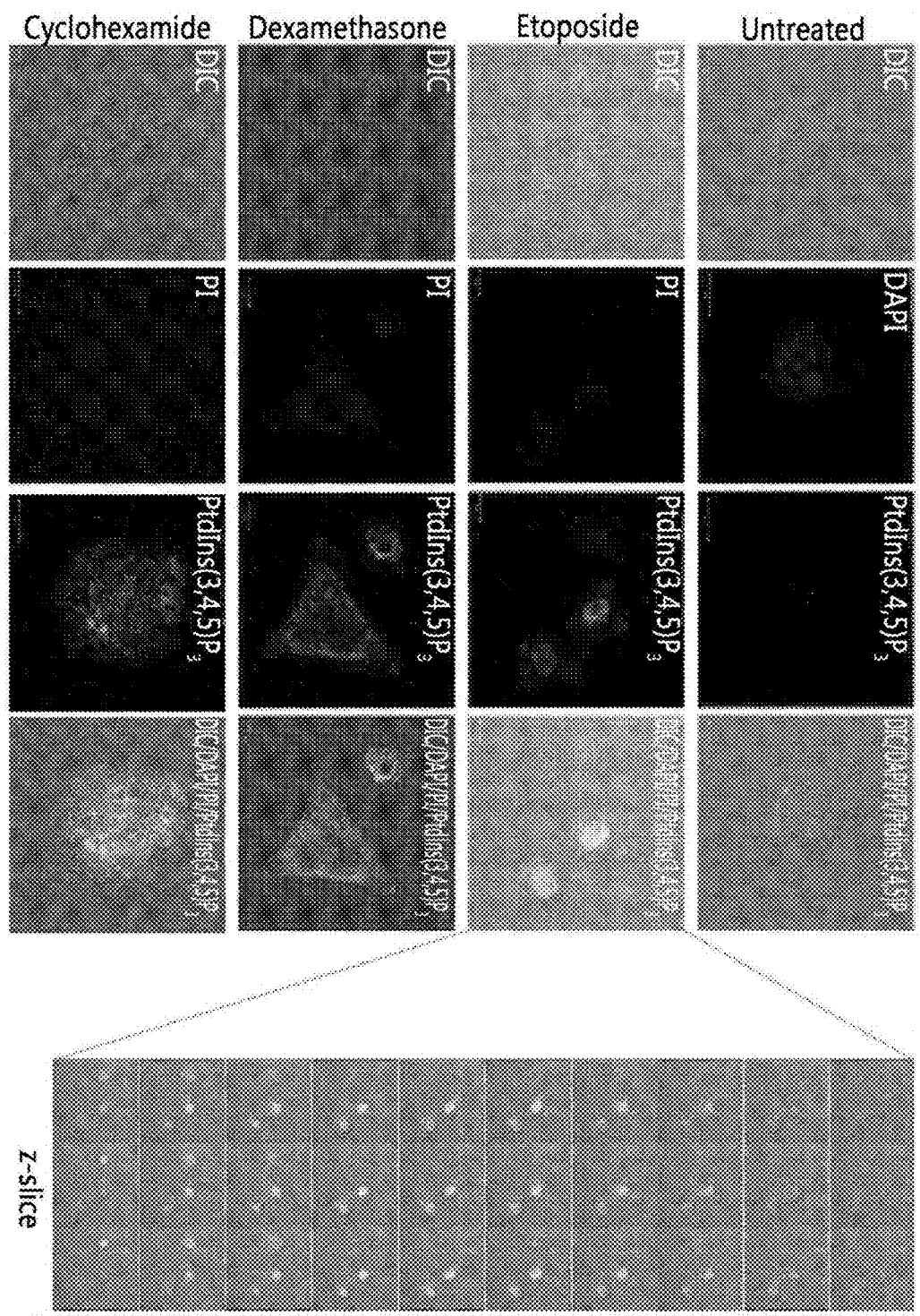

[Fig. 2d]
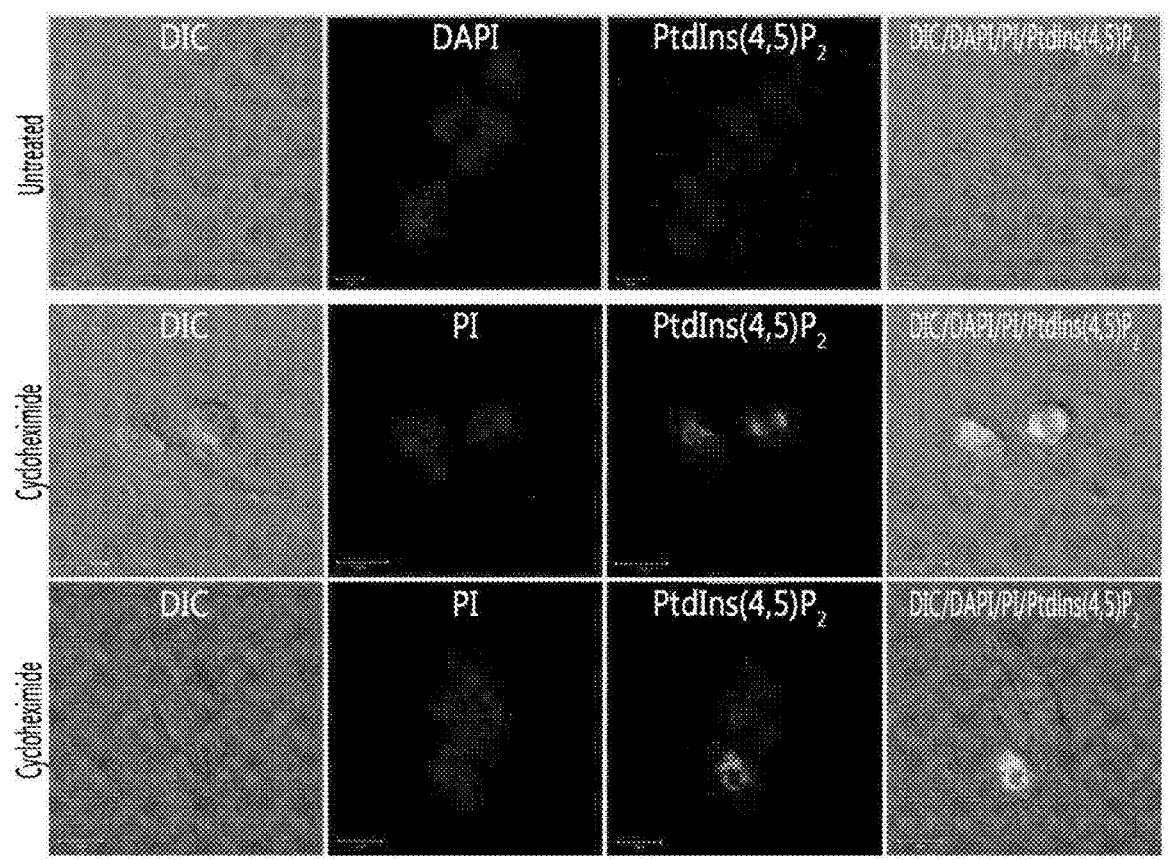

[Fig. 3a]
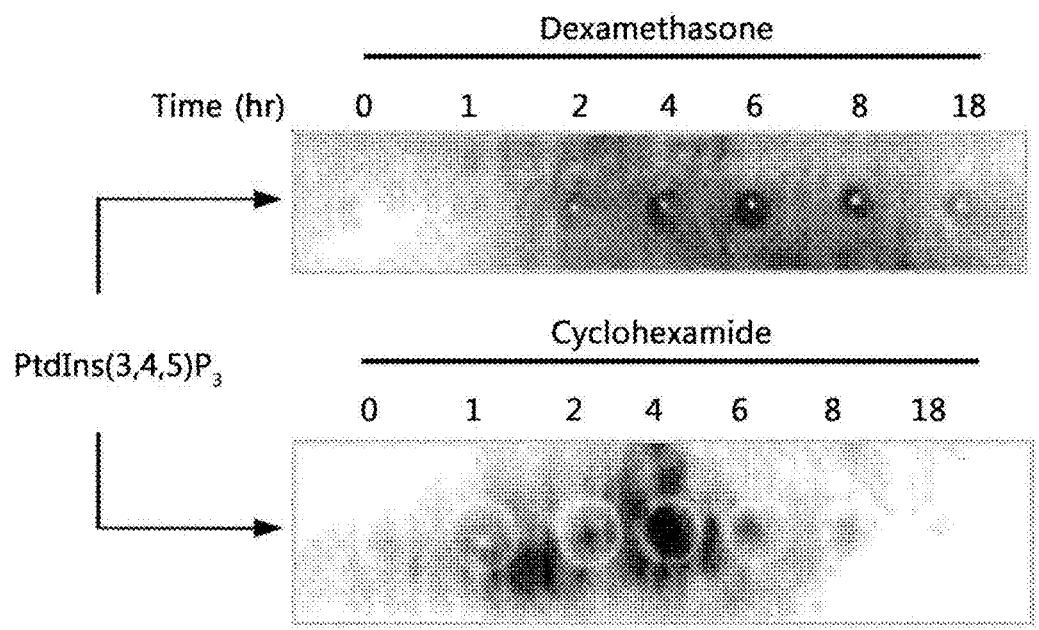
[Fig. 3b]
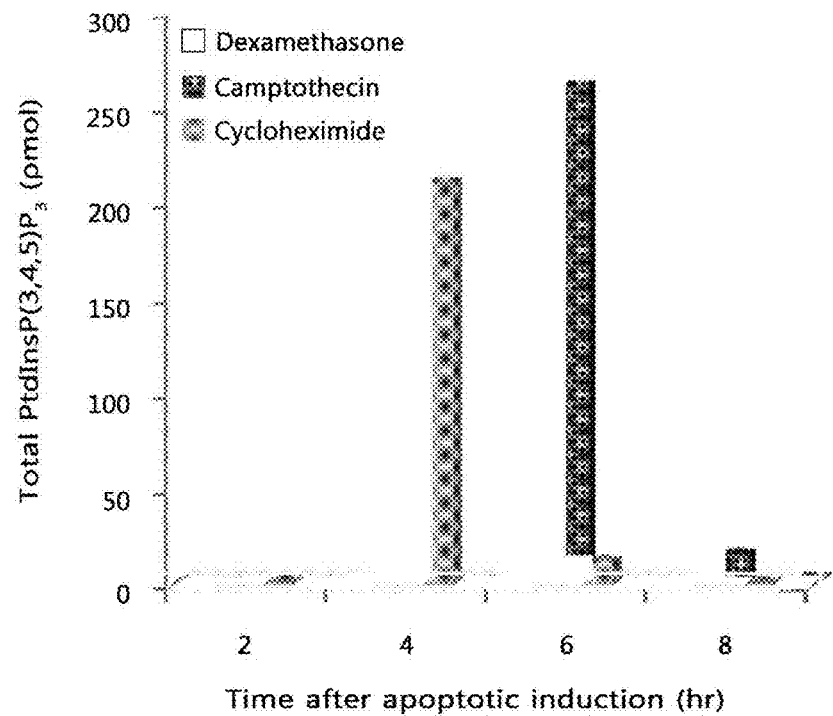

[Fig. 4a]
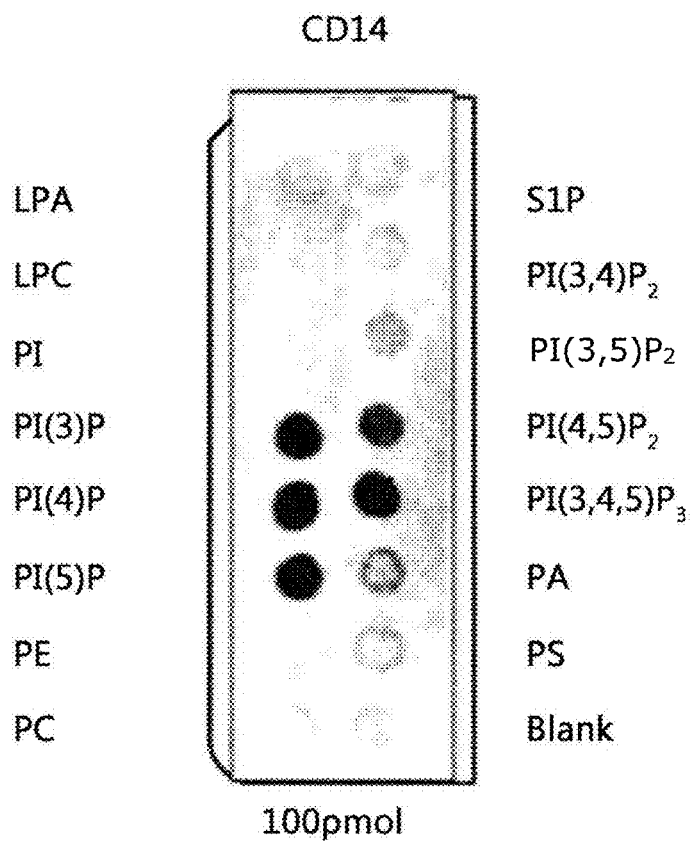
[Fig. 4b]
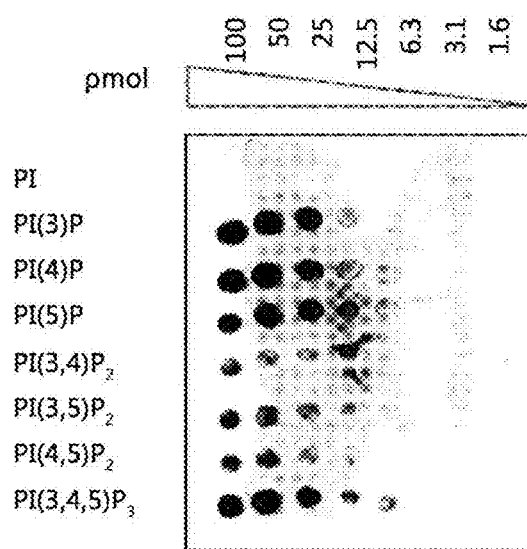

[Fig. 4c]
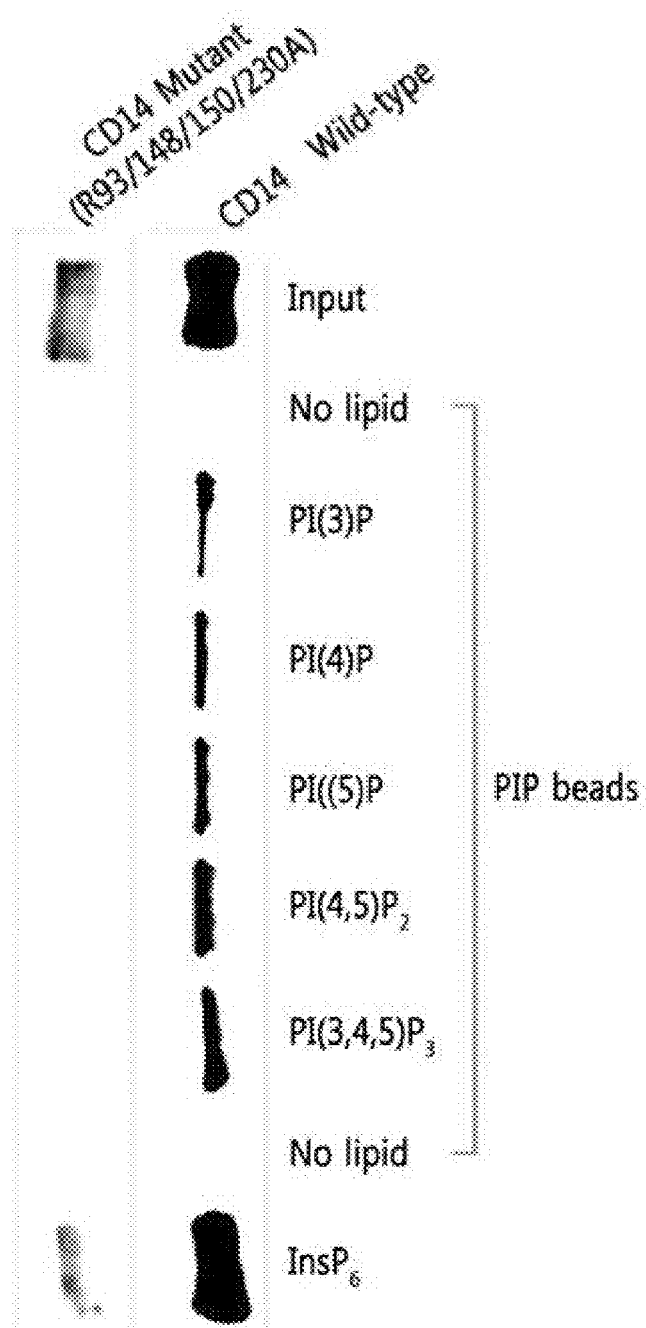

[Fig. 5]
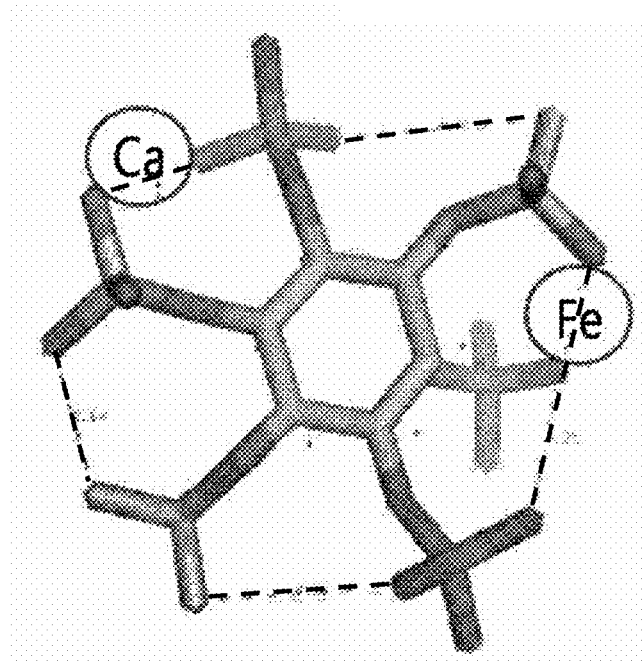

[Fig. 6a]
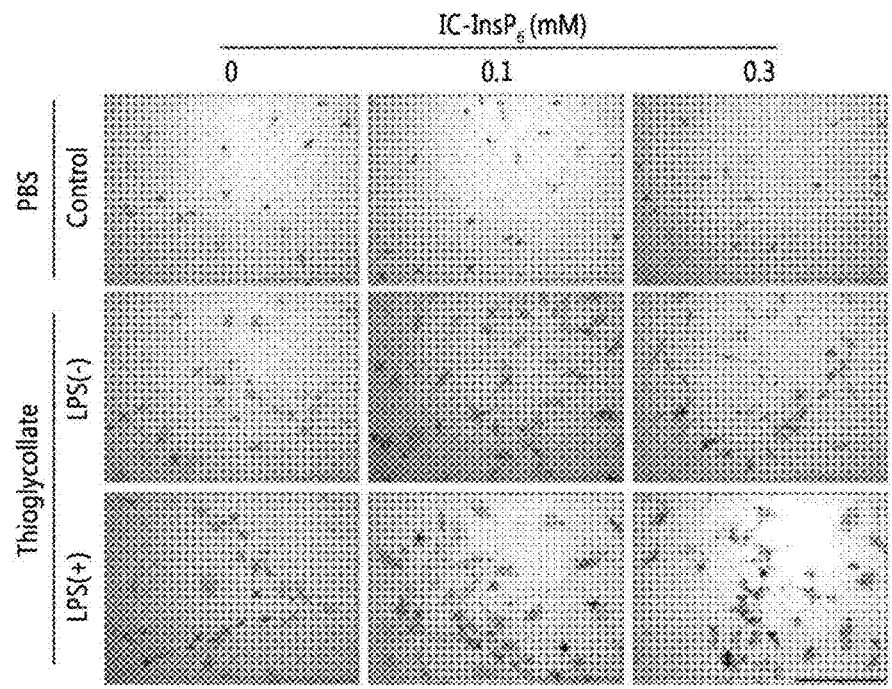
[Fig. 6b]
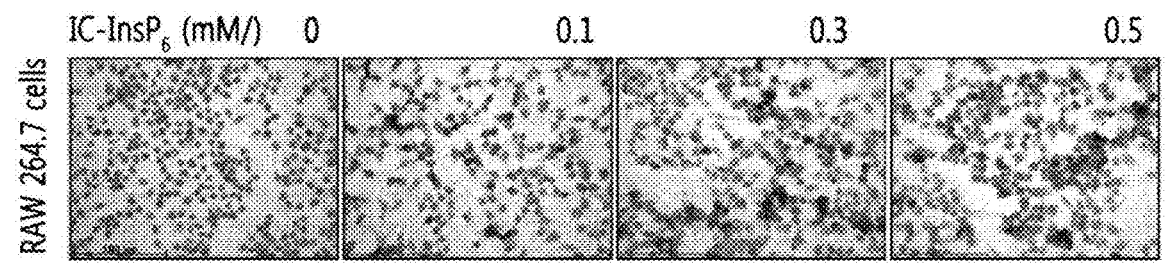

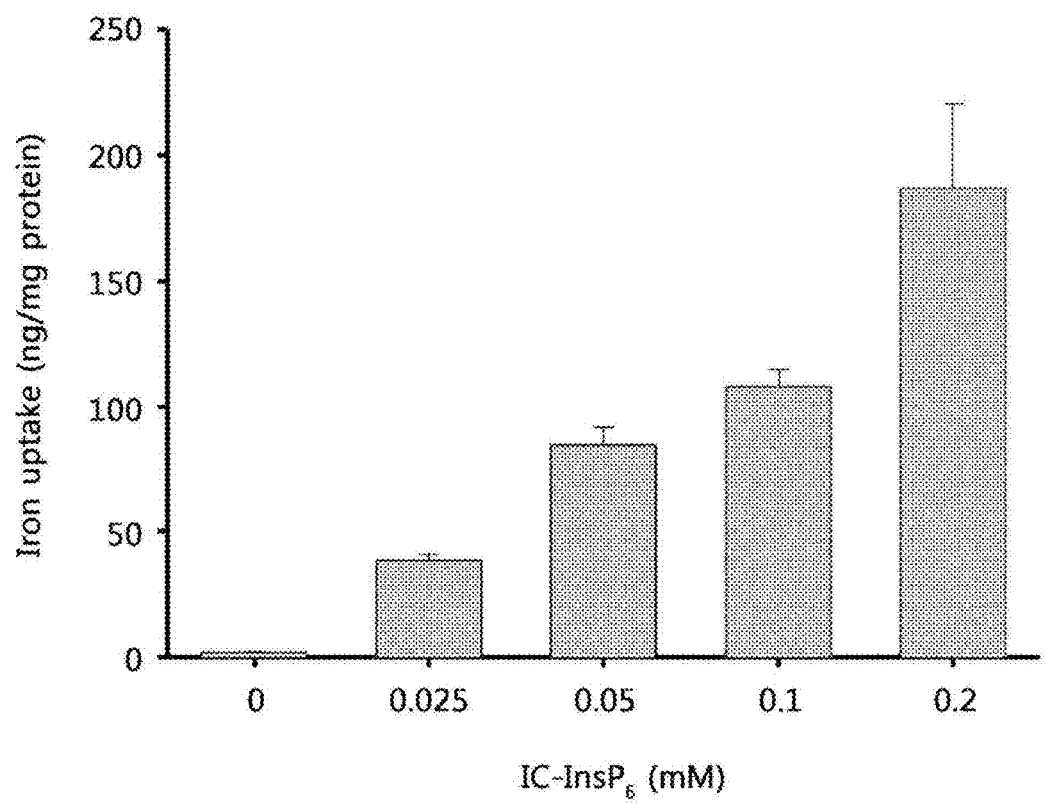
[Fig. 6c]

[Fig. 7a]
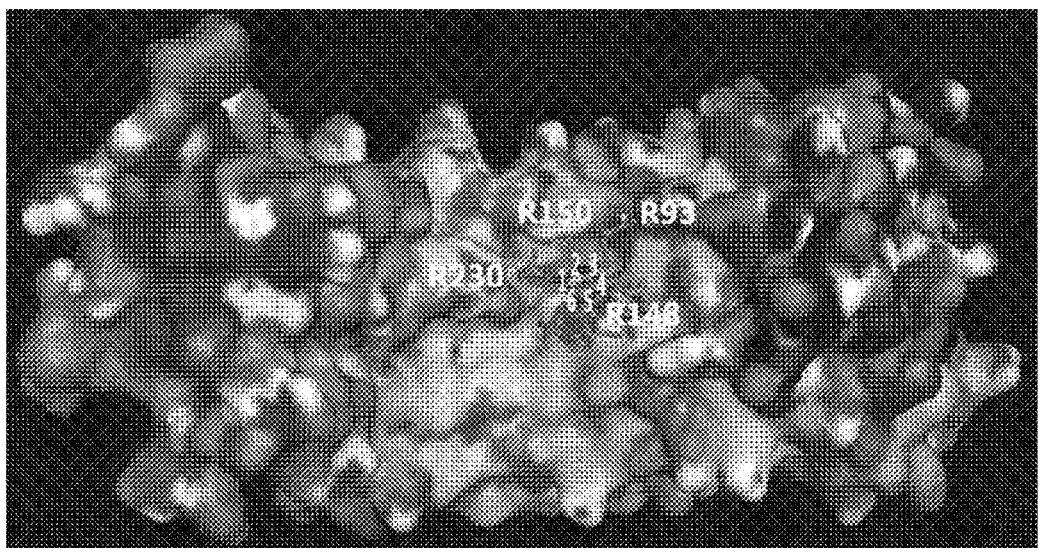

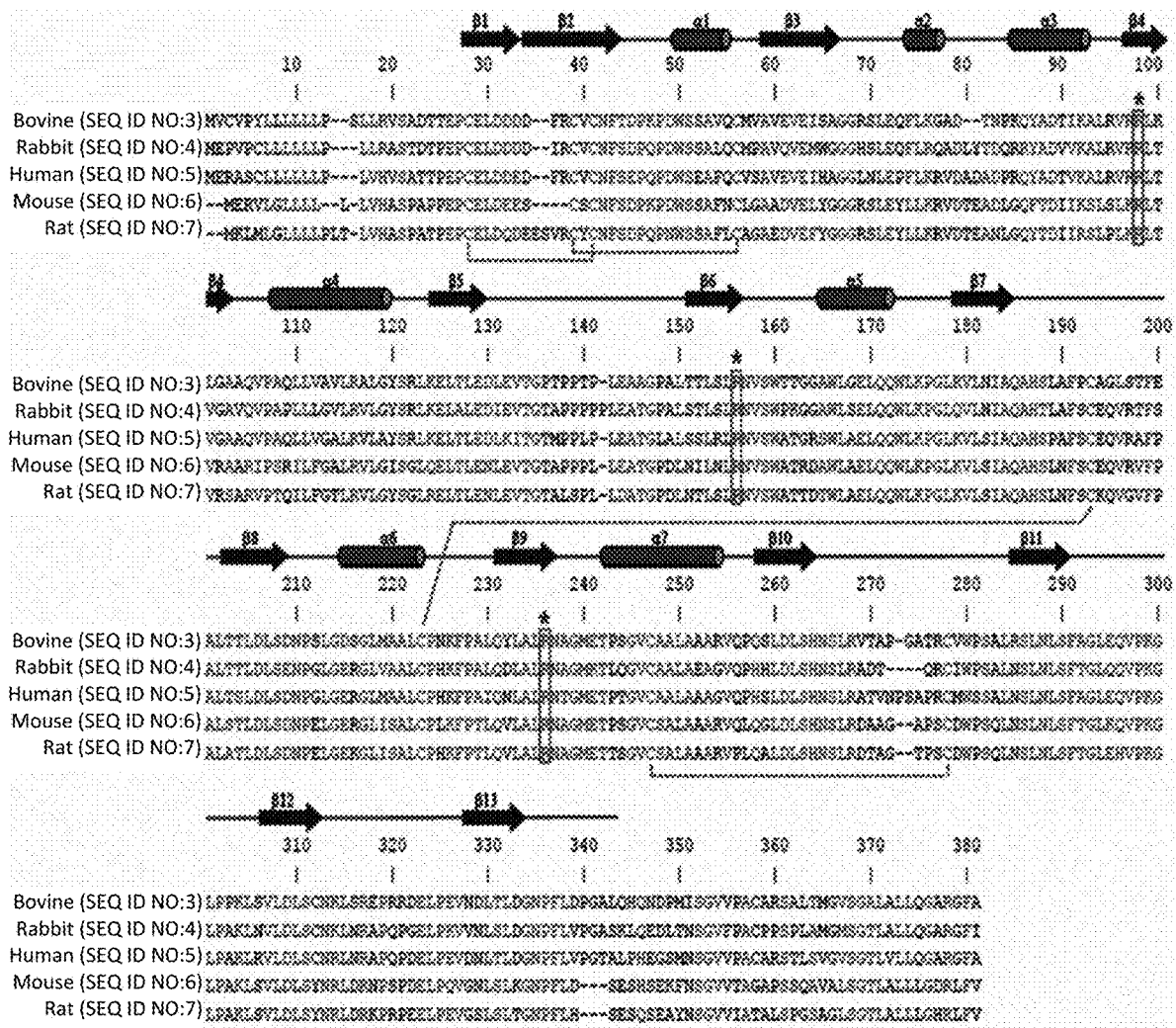
[Fig. 7b]

[Fig. 8]
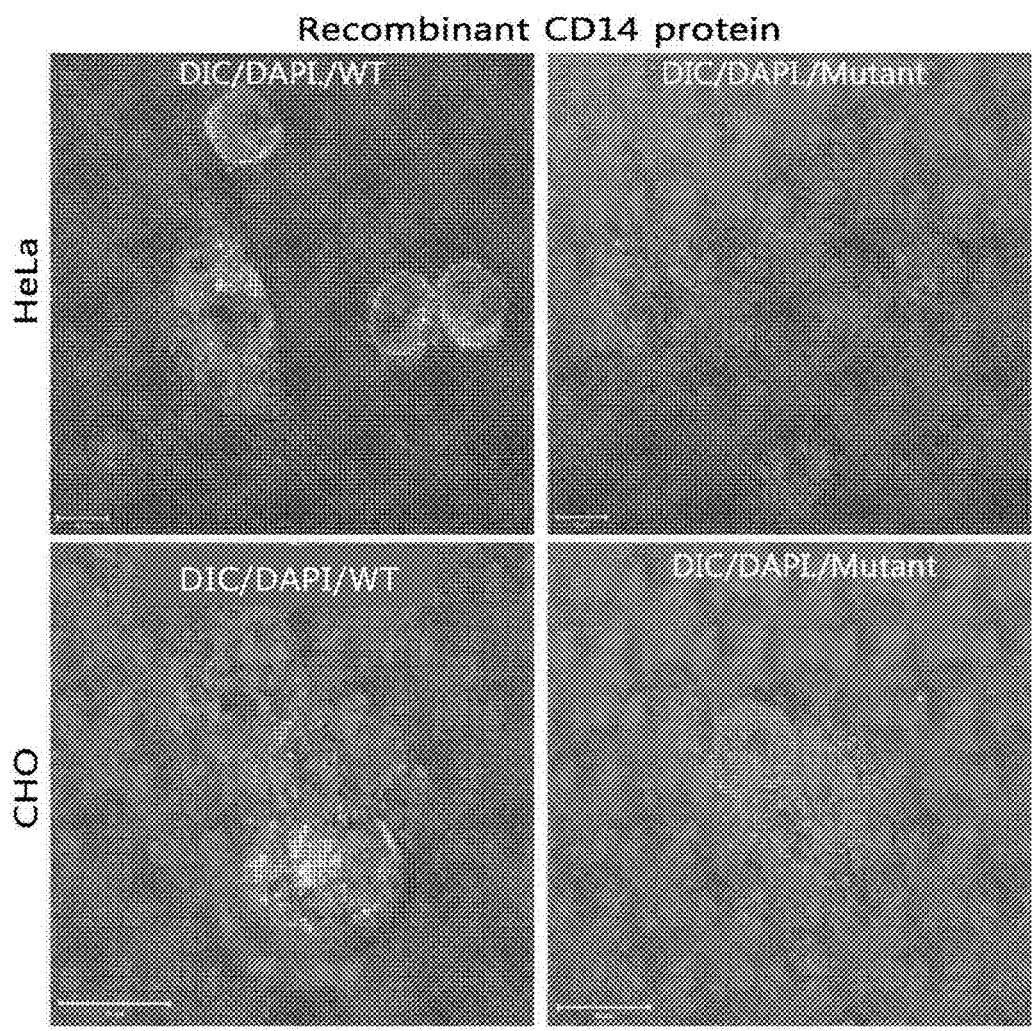

[Fig. 9a]
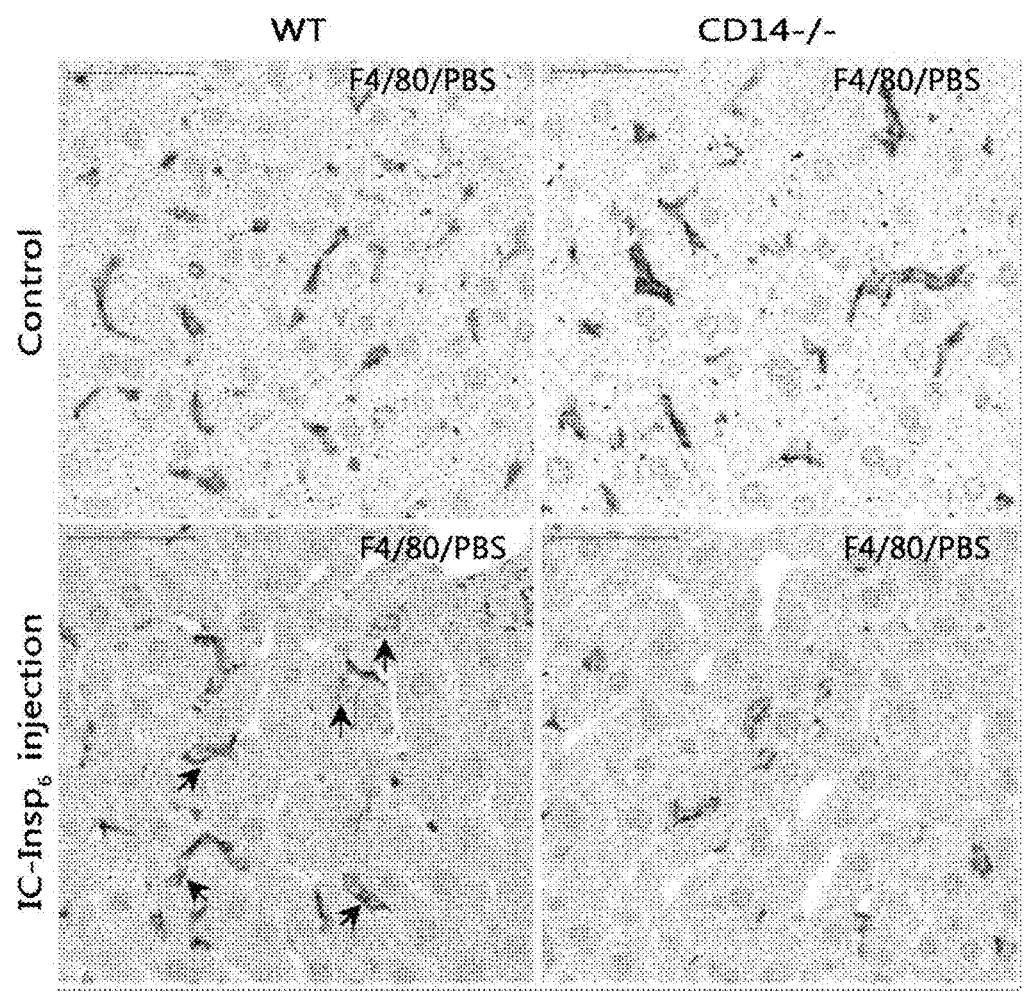

[Fig. 9b]
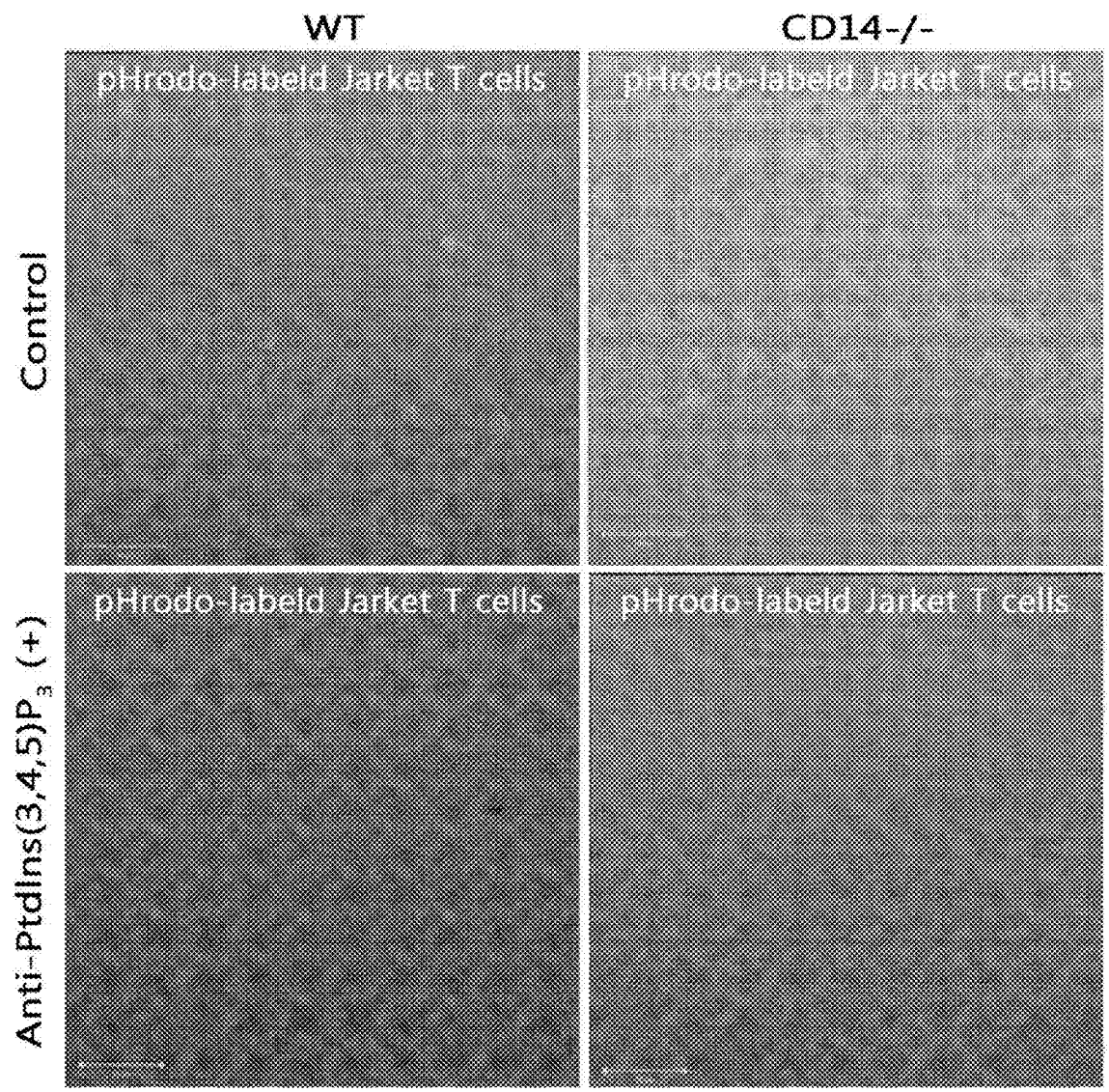

[Fig. 9c]
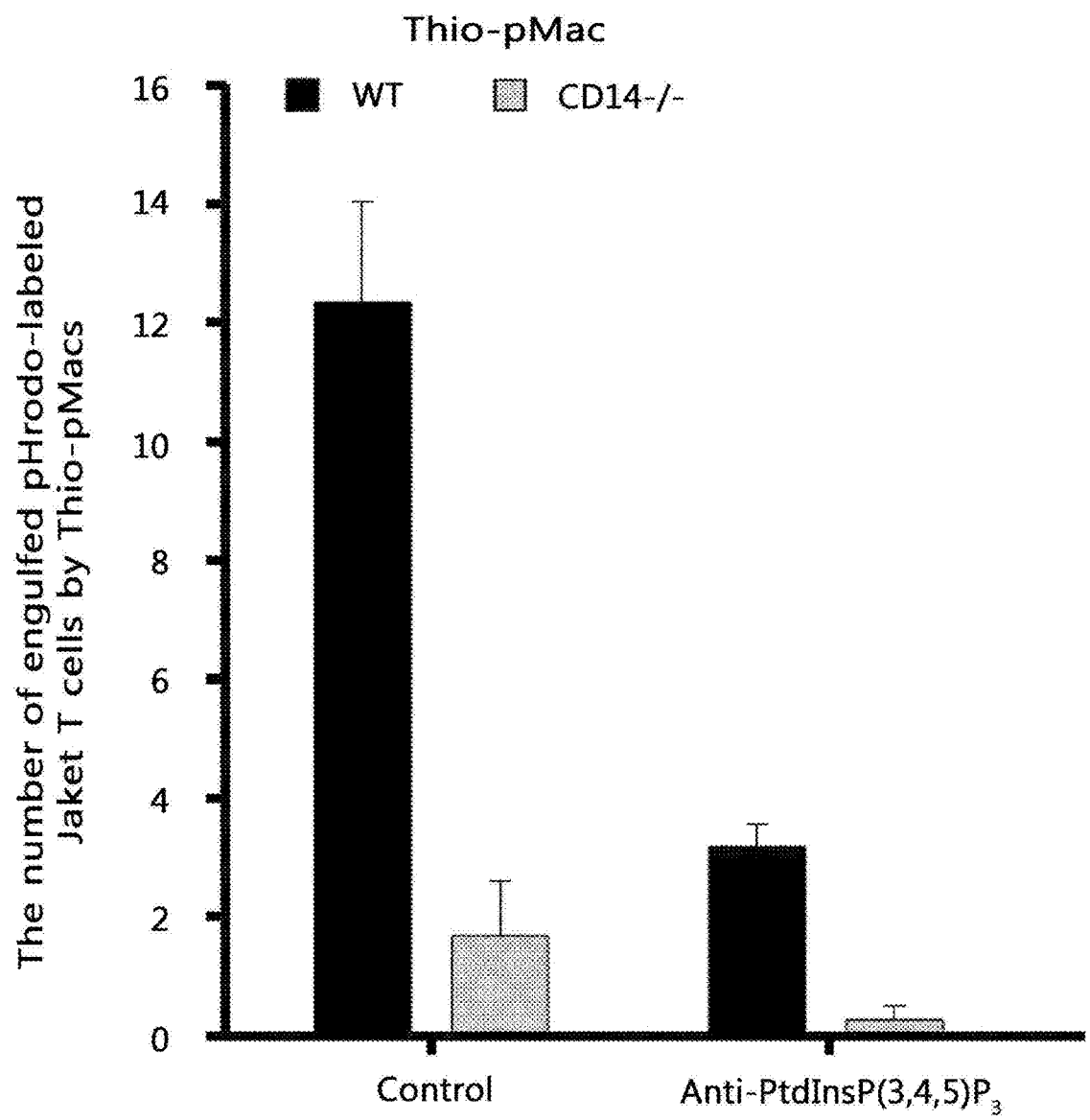

[Fig. 10]
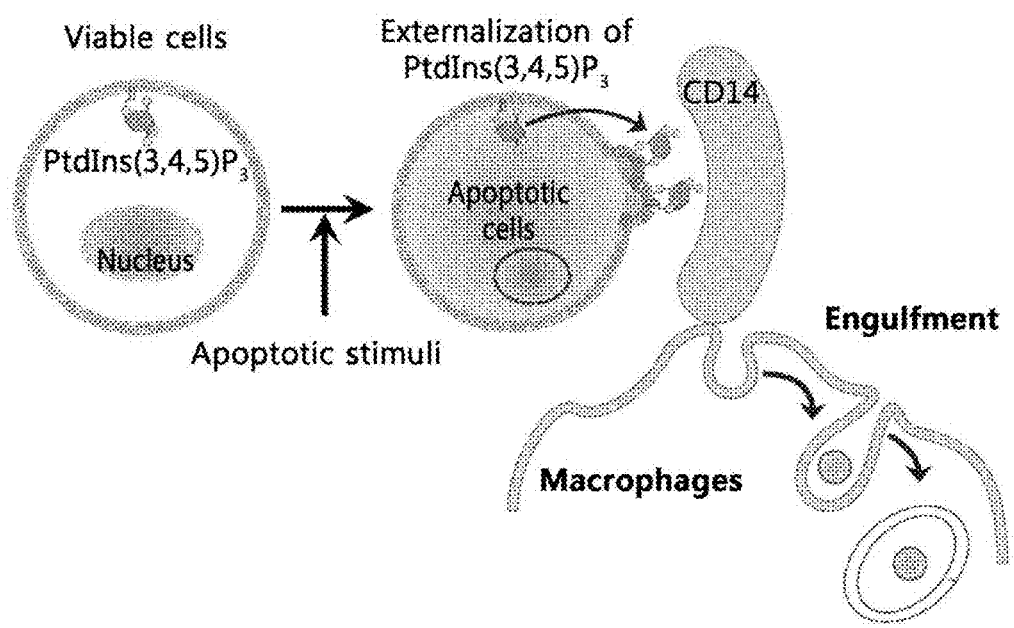

[Fig. 11a]
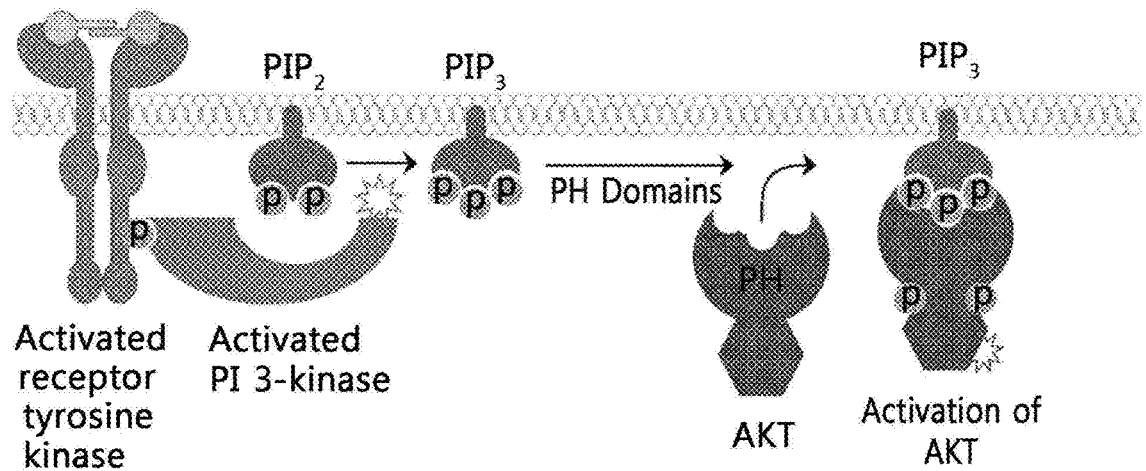

[Fig. 11b]
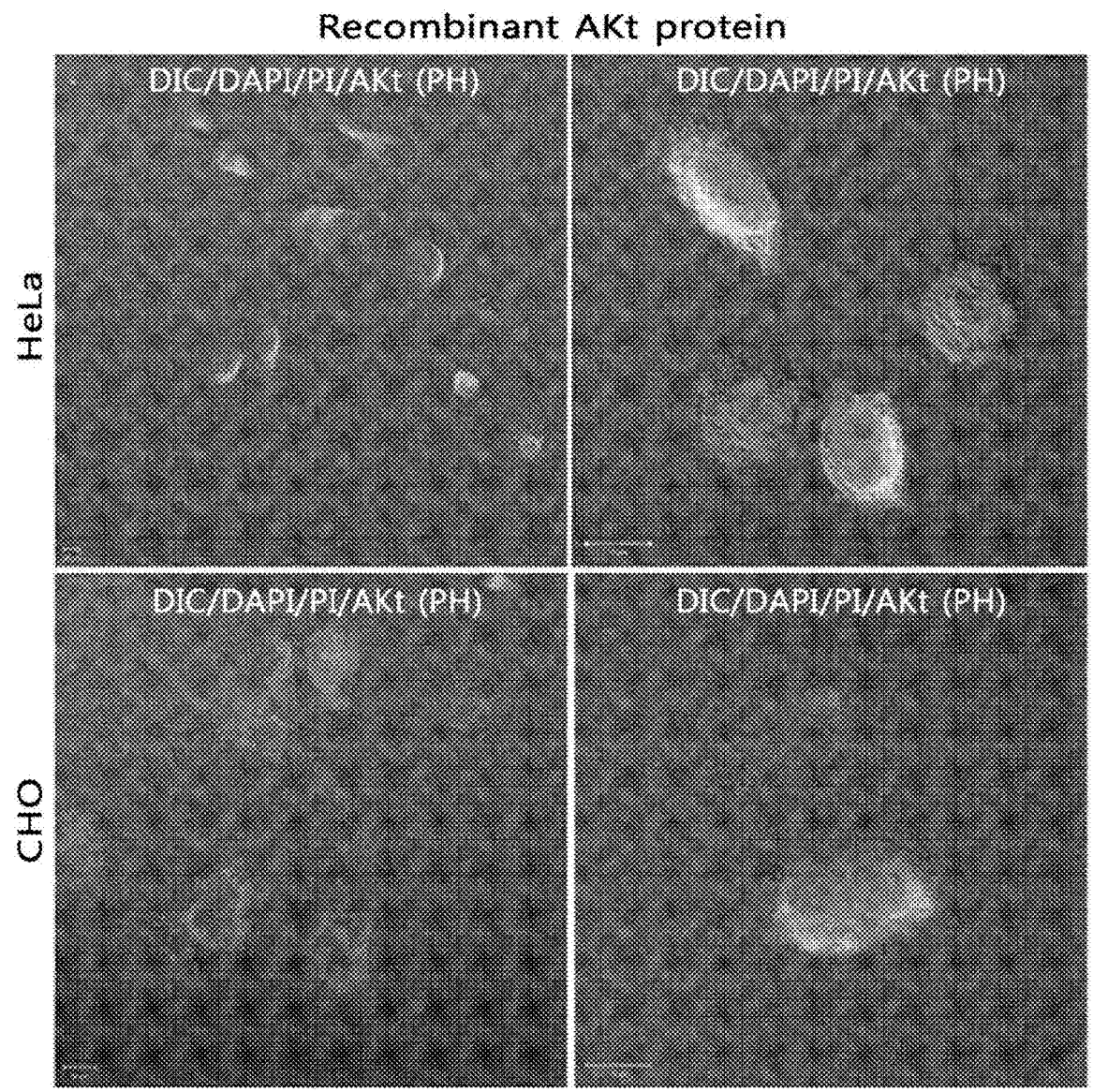

[Fig. 11c]
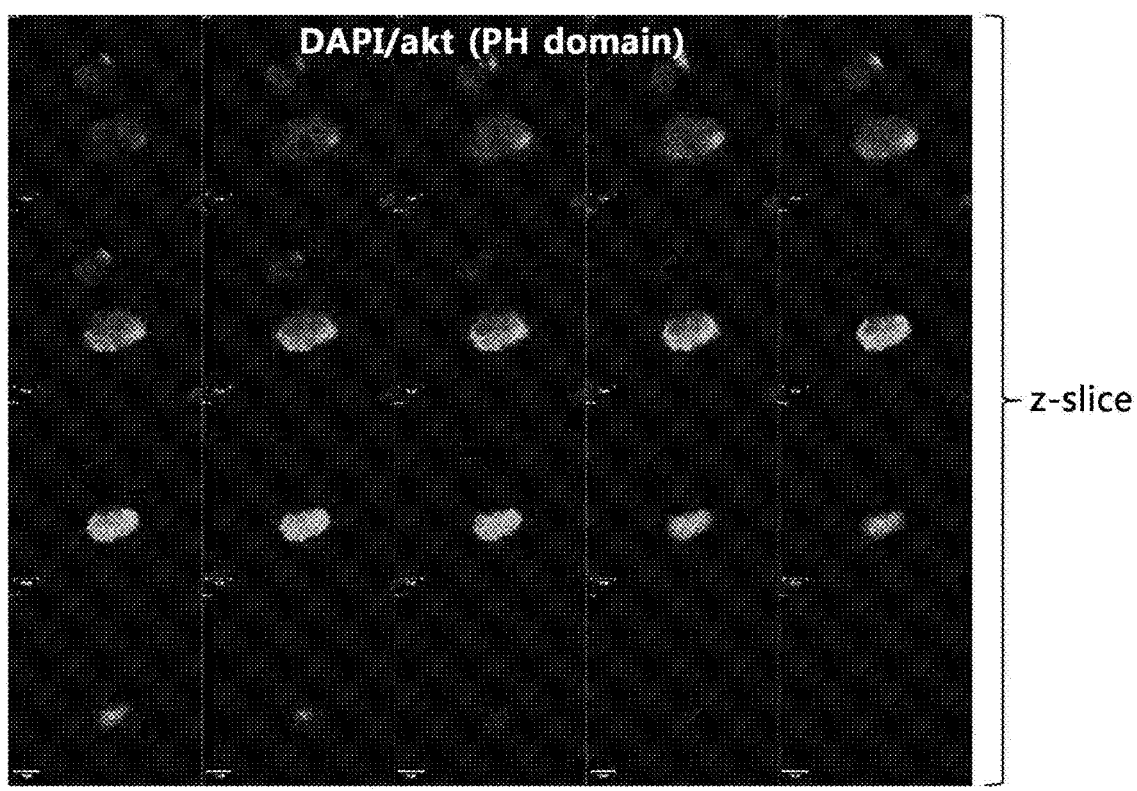

[Fig. 12a]
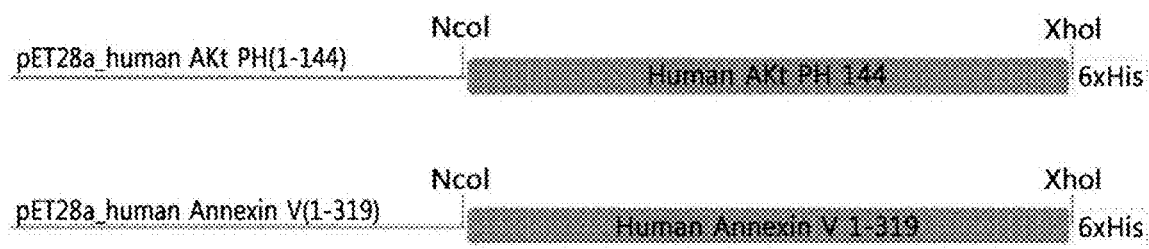

[Fig. 12b]
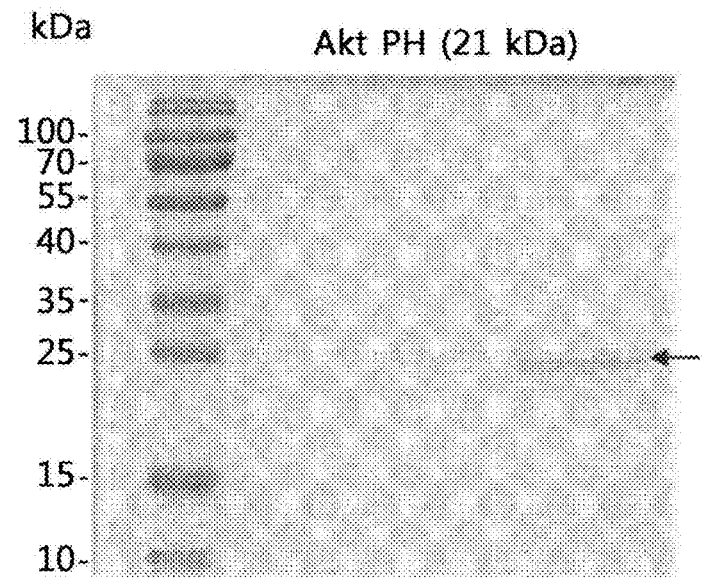
[Fig. 12c]
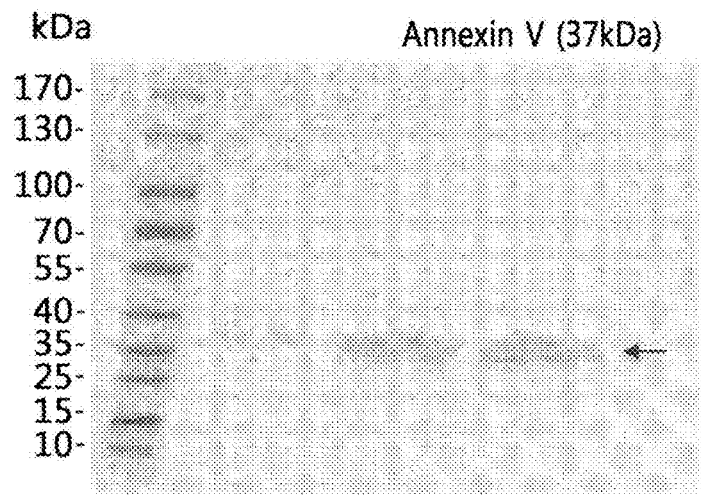

[Fig. 13]
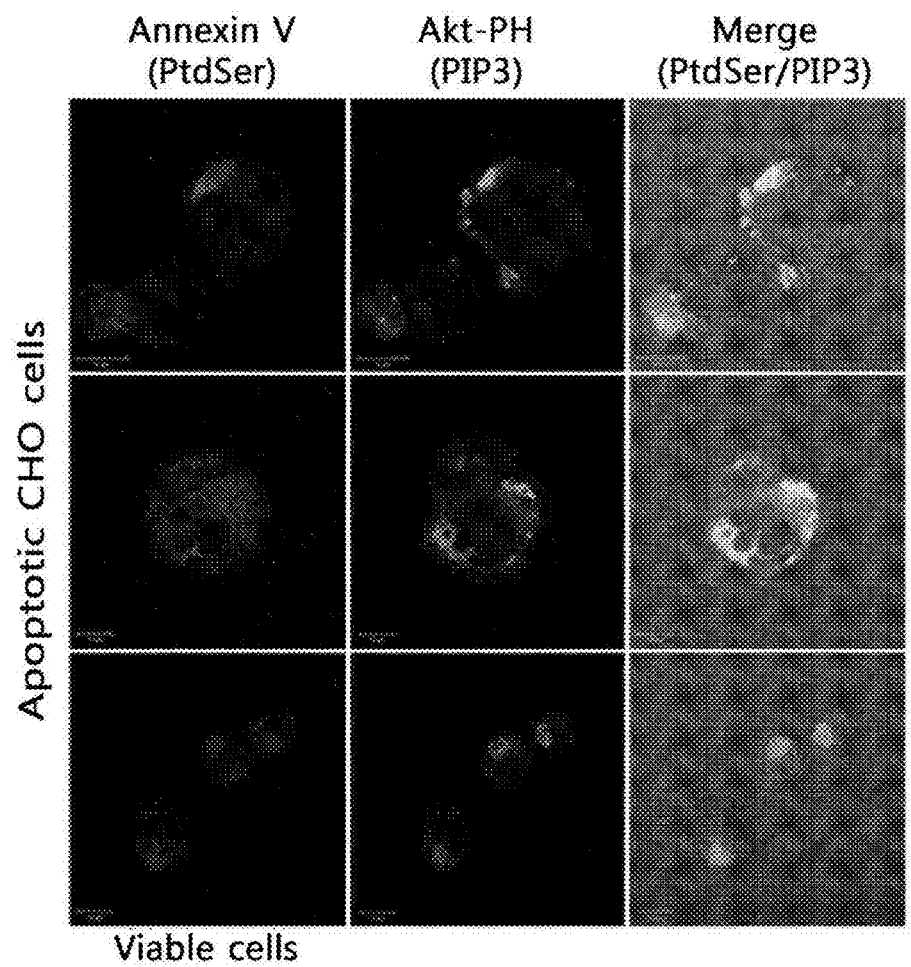

[Fig. 14]
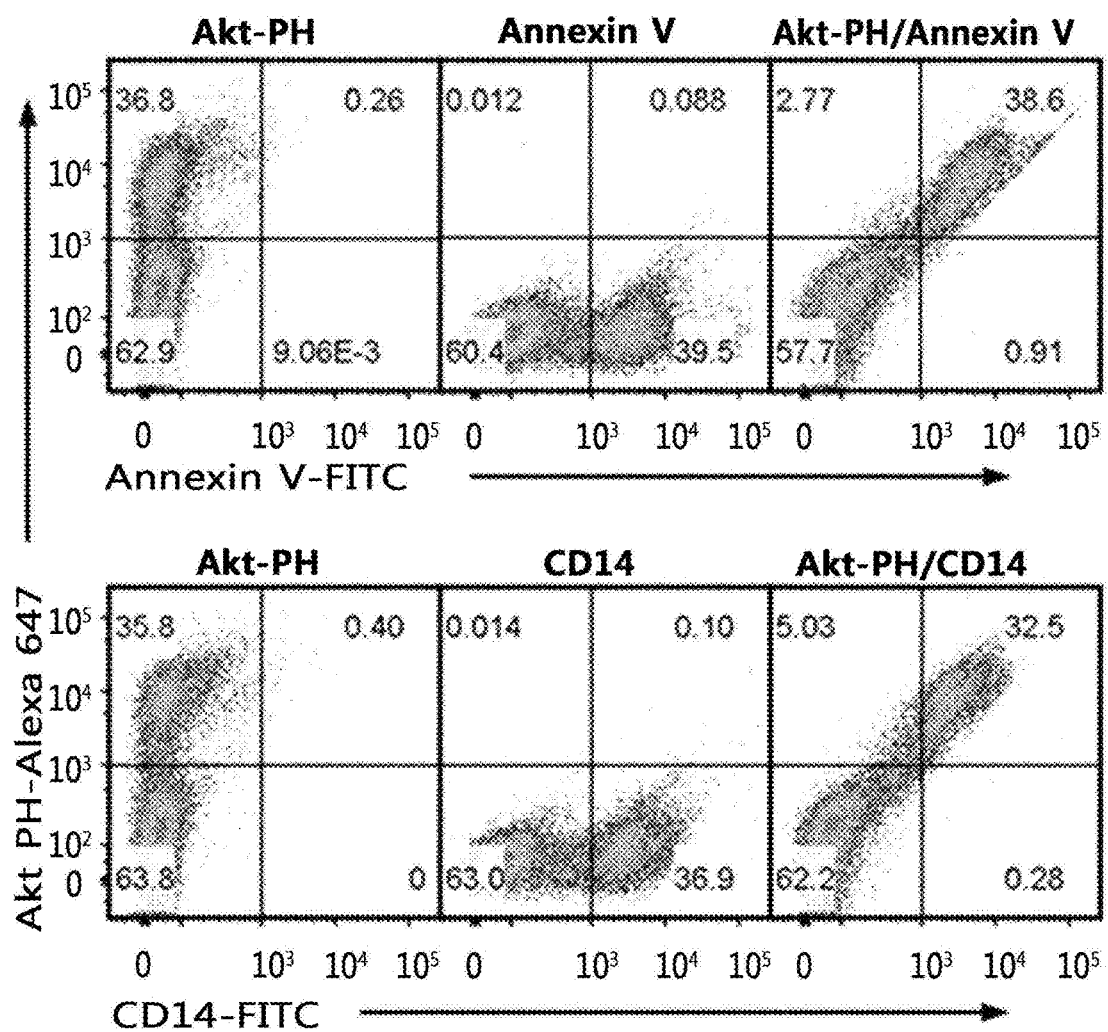

[Fig. 15a]
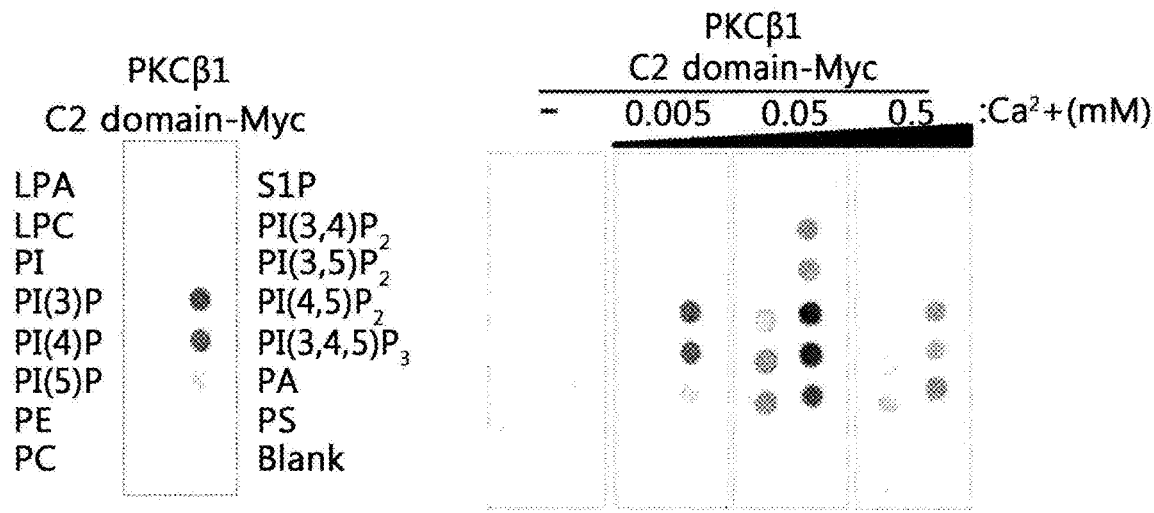
[Fig. 15b]
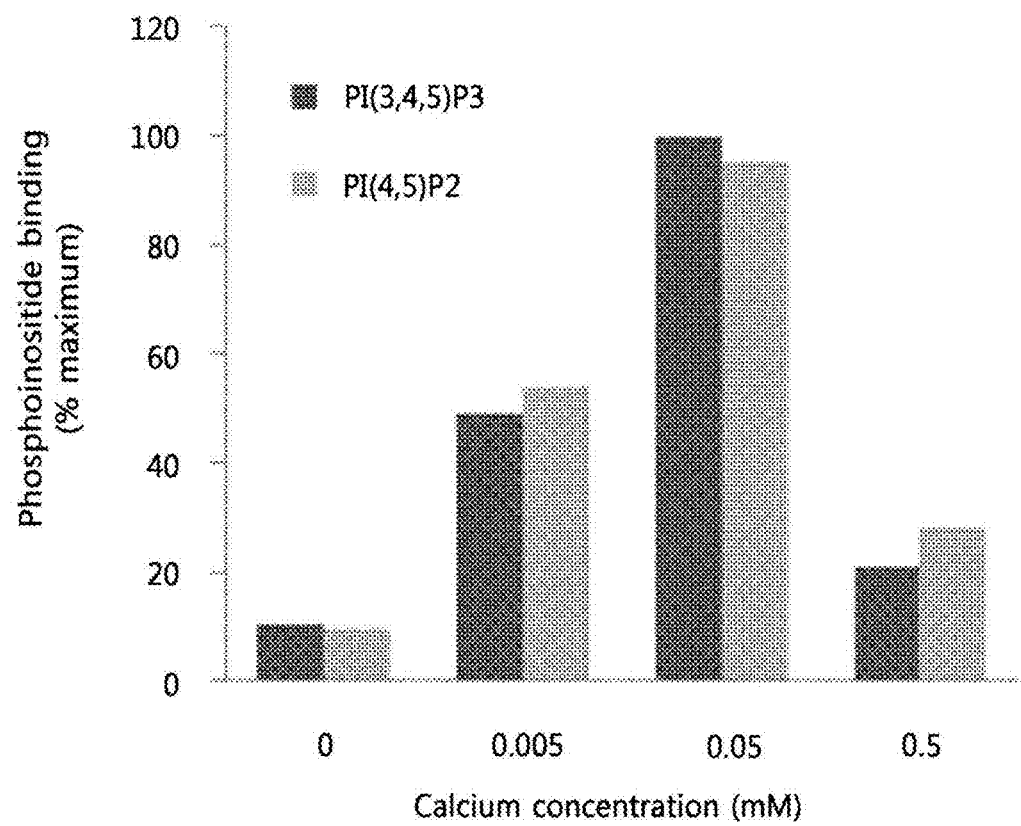

[Fig. 16]
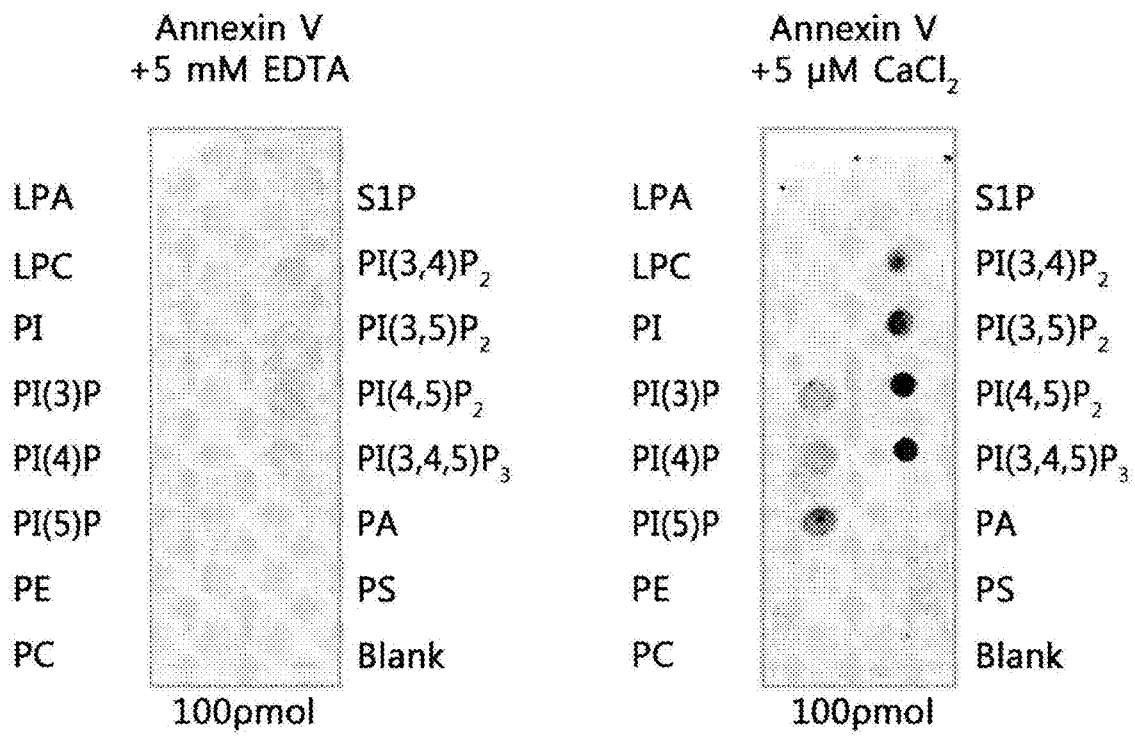

SEQUENCE LISTING

```
<160> NUMBER OF SEQ ID NOS: 2

<210> SEQ ID NO 1
<211> LENGTH: 24
<212> TYPE: DNA
<213> ORGANISM: Artificial Sequence
<220> FEATURE:
<223> OTHER INFORMATION: primer (forward)

<400> SEQUENCE: 1
ttggtgccaa cagatgaggt tcac                                        24

<210> SEQ ID NO 2
<211> LENGTH: 23
<212> TYPE: DNA
<213> ORGANISM: Artificial Sequence
<220> FEATURE:
<223> OTHER INFORMATION: primer (reverse)
```

```
<400> SEQUENCE: 2
ttctttccta cacagcggca ccc                                          23
```

USE OF PHOSPHATIDYLINOSITOL PHOSPHATE-BINDING MATERIAL FOR APOPTOSIS DETECTION

RELATED APPLICATIONS

This application is continuation of International Patent Application No. PCT/KR2016/000673, filed Jan. 21, 2016, which is hereby incorporated by reference in its entirety, and which claims priority to Korean Patent Application No. 10-2015-0010192, filed Jan. 21, 2015.

SEQUENCE LISTING

The sequences listed in the accompanying Sequence Listing are presented in accordance with 37 C.F.R. 1.822. The Sequence Listing is submitted as an ASCII computer readable text file, which is incorporated by reference herein.

TECHNICAL FIELD

The present invention relates to a method for detecting apoptosis using a phosphatidylinositol phosphate-binding material, a method for screening anticancer agents, a method for screening apoptosis-inhibiting materials, and a method for inhibiting phagocytosis.

BACKGROUND ART

Phosphatidylserine (PS) is an important marker by which macrophages can recognize and eliminate apoptotic cells (Schlegel, R. A. et al., *Cell Death and Differentiation*, 2001, 8: 551-563). Normally, phosphatidylserine is present in a cell membrane, but when a cell receives a death signal or red blood cells become old, phosphatidylserine is translocated to the outside of a cell membrane and macrophages recognize the translocated phosphatidylserine via receptors exposed on the cell surface and induce phagocytosis (Fadok, V. A. et al., *J Immunol* 1992, 148:2207-2216).

Annexin V is a protein which can effectively bind to phosphatidylserine (U.S. Patent Application Publication No. 2013-0302827). When the structure of a cell membrane is destroyed in the early stage of apoptosis, the phosphatidylserine that had been exposed only inside a cell becomes exposed to the outside of the cell membrane. Therefore, annexin V-containing kits developed based on the above are widely used for detecting apoptosis. International Patent Publication No. WO 2009107971A2 discloses a composition for detecting apoptosis containing a polypeptide which is specifically coupled to phosphatidylserine.

Meanwhile, according to the analysis of the health insurance data for the last 10 years released by the Health Insurance Review & Assessment Service of Korea, the total number of diabetic patients in Korea is estimated to be about 7.22 million in 2020, which is about one out of seven people in Korea (i.e., 14.4% of the Korean population) (PARK Youngsu, *HANYANG MEDICAL REVIEWS* 29 (2), 2009). Accordingly, a huge socioeconomic loss is expected to follow.

These methods for treating diabetes may include a method using oral hypoglycemic agents and insulin and a transplantation method using the pancreas and islets of Langerhans (KIM, Hwajeong et al., *J Korean Soc Transplant, December* 2009; 23 (3):214-226). Recently, there is a growing interest on the surgeries to recover insulin-secretory function via transplantation of the islets of Langerhans of other people with insulin-secretory function and thus the success rate of the surgery has been improved. The transplantation of the islets of Langerhans is less invasive and more convenient, compared to pancreas transplantation, thus having advantages in that adverse effects due to surgery occur less, hospitalization period becomes shorter, and repeated surgery is possible. Additionally, even when pancreas transplantation is impossible, the transplantation of the islets of Langerhans can be performed by taking them from a donor.

However, when the transplantation is performed according to the Edmonton protocol for islet transplantation widely used at present (Shapiro A M et al., *N Engl J Med* 2006; 355: 1318-30), the instant blood-mediated inflammatory reaction (IBMIR) may occur due to immune responses in the blood vessel thereby inducing the apoptosis of the islets of Langerhans. When cells from two or more donors are used for transplantation, inflammatory responses may be aggravated due to different HLA antigens and it may cause rejections. Therefore, there is a need to develop a therapeutic method for inhibiting apoptosis during the transplantation of the islets of Langerhans.

DISCLOSURE

Technical Problem

Under the circumstances, the present inventors have made efforts to develop a method for detecting apoptosis using a labeling material, which appears in apoptotic cells, and protecting apoptotic cells from phagocytosis. As a result, the present inventors have discovered that, upon induction of apoptosis, phosphatidylinositol phosphates are externalized to the surface of apoptotic cells and macrophages can thereby recognize the apoptosis via CD14 receptors. Accordingly, a material capable of effectively binding to phosphatidylinositol phosphates can be used for detecting apoptosis, protecting apoptosis, and screening anticancer agents, thereby completing the present invention.

Technical Solution

A main object of the present invention is to provide a composition for detecting apoptosis containing a phosphatidylinositol phosphate-binding material.

Another object of the present invention is to provide a kit for detecting apoptosis including the composition for detecting apoptosis.

Still another object of the present invention is to provide a method for detecting apoptosis, which includes a first step of treating a cell-containing sample with the composition for detecting apoptosis; and a second step of detecting a labeling material from the sample.

Still another object of the present invention is to provide a composition for screening anticancer agents, including the composition for detecting apoptosis.

Still another object of the present invention is to provide a method for screening anticancer agents, which includes a first step of treating a cancer cell-containing sample with the composition labeled with a labeling material for screening anticancer agents and a candidate material thereof; and a second step of detecting a labeling material from the sample.

Still another object of the present invention is to provide a method for screening apoptosis-inhibiting materials, which includes a first step of treating a cell-containing sample with the composition labeled with a labeling material for screening apoptosis-inhibiting materials and a candidate material for inhibiting apoptosis; a second step of inducing the apoptosis of the cell; and a third step of quantifying the labeling material from the sample.

Still another object of the present invention is to provide a composition for inhibiting phagocytosis, containing a phosphatidylinositol phosphate-binding material.

Still another object of the present invention is to provide a method for inhibiting phagocytosis, which includes treating cells, tissues, or organs with the composition for inhibiting phagocytosis.

Advantageous Effects of the Invention

The composition and kit for detecting apoptosis and a method for detecting apoptosis according to the present invention can easily detect the occurrence and level of apoptosis using a phosphatidylinositol phosphate-binding material.

Using the above, the present invention can easily screen anticancer agents or apoptosis-inhibiting materials, protect cells by inhibiting phagocytosis, and reduce side-effects that may occur during transplantation.

BRIEF DESCRIPTION OF DRAWINGS

FIG. 1a shows a schematic diagram illustrating a pleckstrin homology (PH) domain, which binds to phosphatidylinositol phosphate, a CD14, and a capping by the same; FIG. 1b shows a schematic diagram illustrating the externalization of phosphatidylinositol phosphate according to the treatment of an apoptosis-inducing agent and preparation of phosphatidylinositol phosphate according to the same; and FIG. 1c shows a schematic diagram illustrating the binding of the externalized phosphatidylinositol phosphate to macrophages activated via CD 14.

FIGS. 2a to 2d show the externalization of phosphatidylinositol phosphate according to the treatment with an apoptosis-inducing agent, in which FIG. 2a shows the PtdIns(3,4,5)P$_3$ externalized at the early stage of apoptosis; FIG. 2b shows the PtdIns(3,4,5)P$_3$ externalized at the secondary necrosis; FIG. 2c shows the externalization of PtdIns (3,4,5)P$_3$ according to the treatment with an apoptosis-inducing agent; and FIG. 2d shows the externalized PtdIns (4,5)P$_2$.

FIG. 3a shows the concentration of total PdtIns(3,4,5)P$_3$ of Jurkat T cells according to time and FIG. 3b shows the graphs illustrating the concentration of total PdtIns(3,4,5)P$_3$ of HeLa cells according to time.

FIGS. 4a and 4b show the results of a protein-lipid assay and immunoblotting and FIG. 4c shows the results of PIP-affinity bead pulldowns.

FIG. 5 shows the chemical structure of IC-InsP$_6$.

FIG. 6a shows IC-InsP6 absorbed by peritoneal macrophages and FIGS. 6b and 6c show IC-InsP$_6$ absorbed by RAW264.7 macrophages.

FIG. 7a shows an image illustrating the binding between the 1-, 3-, 4-, 5-phosphate groups of PtdIns(3,4,5)P$_3$ and R93, R148, R150, and R230 amino acid residues of CD14, and FIG. 7b shows a schematic diagram illustrating the amino acid residues conserved between species.

FIG. 8 shows the binding between a wild-type recombinant CD14 receptor or modified CD14 receptor and PtdIns (3,4,5)P$_3$.

FIG. 9a shows the phagocytosis of the liver Kupffer cells of a CD14-defective mouse and a wild-type mouse, and FIGS. 9b and 9c show the phagocytosis of pHrodo-labeled apoptotic cells of macrophages of a CD14-defective mouse and a wild-type mouse.

FIG. 10 shows a schematic diagram illustrating the role of the PdtIns(3,4,5)P$_3$ externalized on the surface of apoptotic cells.

FIG. 11a shows a schematic diagram illustrating the action of the Akt protein, and FIGS. 11b and 11c show the binding between the PH domain of a recombinant Akt protein and the PtdIns(3,4,5)P$_3$ externalized on the surface of apoptotic cells.

FIG. 12a shows pET28a which includes a human Akt PH domain; FIG. 12b shows a prepared and confirmed recombinant PH domain; and FIG. 12c a prepared and confirmed recombinant annexin V.

FIG. 13 shows the externalized PtdIns(3,4,5)P$_3$, to which the PH domain binds; and PdtSer, to which annexin V binds, obtained using a laser-scanning confocal microscope.

FIG. 14 shows the externalized PtdIns(3,4,5)P$_3$, to which the PH domain or CD14 protein binds; and PdtSer, to which annexin V binds, obtained using a flow cytometer.

FIG. 15a shows the results of a protein-lipid assay and immunoblotting with respect to a C2 domain protein, and FIG. 15b shows the graphs illustrating the statistical analysis of the results shown on the right of FIG. 15a.

FIG. 16 shows the results of a protein-lipid assay and immunoblotting with respect to annexin V.

The error bars in each graph of the above figures are represented by mean±standard deviation of at least 3 independent experiments. The statistical significance between groups was determined by student t-test and $P<0.05$ was considered to be statistically significant.

BEST MODE

To achieve the above objects, in an aspect, the present invention provides a method for detecting apoptosis which includes a phosphatidylinositol phosphate-binding material.

In another aspect, the present invention provides a method for screening anticancer agents, which includes: a first step of treating a cancer cell-containing sample with a phosphatidylinositol phosphate-binding material labeled with a labeling material and a candidate material thereof; and a second step of detecting a labeling material from the sample.

In still another aspect, the present invention provides a method for screening apoptosis-inhibiting materials, which includes: a first step of treating a phosphatidylinositol phosphate-binding material and an apoptosis-inhibiting material with a cell-containing sample; a second step of inducing the apoptosis of the cells of the first step; and a third step of quantifying a labeling material from the sample.

In still another aspect, the present invention provides a method for inhibiting phagocytosis including treating cells, tissues, or organs with a composition containing a phosphatidylinositol phosphate-binding material.

A Composition and Kit for Detecting Apoptosis and a Method for Apoptosis Detection To achieve the above objects, in an aspect, the present invention provides a composition for detecting apoptosis including a phosphatidylinositol phosphate-binding material.

Phosphatidylinositol phosphates (PtdInsPs) are materials located in the cytoplasmic layer of a cell membrane, consisting of myo-inositol phosphate, such as Ins(1,4,5)P$_3$ and Ins(1,3,4,5)P$_4$, and diacylglycerol. Phosphatidylinositol phosphates, which are anchors in the cytoplasm that attracts the PIP-binding domain of an effector protein and also protein activators that amplify a signaling induced by various stimuli, have the role of providing an on/off switch in a biological circuit (L. C. Cantley, *Science* 296, 1655, 2002).

However, nothing has been known with respect to phosphatidylinositol phosphates, phagocytosis of macrophages, and recognition of apoptosis.

The present inventors are the first to discover that phosphatidylinositol phosphates are externalized in apoptotic cells (FIGS. 1b, 2a, 2b, and 2d) and the CD14 receptors of macrophages and phosphatidylinositol phosphates thus can specifically bind to each other thereby capable of recognizing apoptosis. Accordingly, apoptosis can be effectively detected using a material which can specifically bind to phosphatidylinositol phosphates.

The phosphatidylinositol phosphate may be phosphatidylinositol-3-phosphate (PtdIns(3)P), phosphatidylinositol-4-phosphate (PtdIns(4)P), phosphatidylinositol-5-phosephate (PtdIns(5)P), phosphatidylinositol-3,4-biphosphate (PtdIns(3,4)P$_2$), phosphatidylinositol-3,5-biphosphate (PtdIns(3,5)P$_2$), phosphatidylinositol-4,5-biphosphate (PtdIns(4,5)P$_2$), or phosphatidylinositol-3,4,5-triphosphate (PtdIns(3,4,5)P$_3$). In an exemplary embodiment of the present invention, it was confirmed that the induction of apoptosis specifically causes the externalization of PtdIns(3,4,5)P$_3$ and PtdIns(4,5)P$_2$ thereby acting as a signal for apoptosis (FIGS. 2a to 2d).

The phosphatidylinositol phosphate-binding material may be one that includes CD14 protein or a variant thereof. The sequence of the CD14 protein is known in the art. In an exemplary embodiment according to the present invention, CD14 has shown a strong binding affinity with the strength of 6.3 pmol for various phosphatidylinositol phosphates but CD14 has shown no affinity for phosphatidylserine, phosphatidylcholine, and sphingosine-1-phosphate (FIGS. 4a and 4b). These results suggest that phosphatidylinositol phosphates having an inositol phosphpate group can be detected using CD14 protein. Additionally, as a result of the PIP-affinity bead pulldowns, it was confirmed that, in the case of CD14 protein, which was modified not to bind to phosphatidylinositol phosphates, the protein did not bind to PIP beads, whereas, in the case of wild-type CD14 protein, the protein was bound to PtdIns(3)P, PtdIns(4)P, PtdIns(5)P, PtdIns(4,5)P$_2$, and PtdIns(3,4,5)P$_3$ (FIG. 4c).

The variant of the CD14 protein may be any protein which has an amino acid sequence having a similarity of 70% or higher, specifically 80% or higher, more specifically 90% or higher, even more specifically 95% or higher, and most specifically, 98% or higher to that of the CD14 protein, and also has a substantial activity capable of binding to PtdIns(3,4,5)P$_3$. It is obvious that any amino acid sequence, which has a biological activity substantially the same as or corresponding to that of the protein having the amino acid sequence of the CD14 protein, as a sequence having the above similarity, should also belong to the scope of the present disclosure, although the amino acid sequence may have deletion, modification, substitution, or addition, in part of the sequence. Additionally, the variants may be one having codon optimization according to the host cell for expression.

For example, the variants of the CD14 protein may be those having R93, R148, R150, and R230 residues, which are the 93$^{rd}$, 148$^{th}$, 150$^{th}$, and 320$^{th}$ arginine residues in the amino acid sequence of human (*Homo sapiens*) CD14 protein. In an exemplary embodiment of the present invention, the absorption of phosphatidylinositol phosphates and inositol-6-phosphate (InsP$_6$), which behaves by mimicking the phosphatidylinositol phosphate, by peritoneal macrophages was evaluated. As a result, it was confirmed that 1-, 3-, 4-, 5-phosphate groups of InsP$_6$ or PtdIns(3,4,5)P$_3$ are fixed by R93, R148, R150, and R230 amino acid residues of CD14 and a salt bridge (FIG. 7a). Accordingly, the CD14 protein which includes R93, R148, R150, and R230 amino acid residues can detect apoptosis by recognizing and binding to phosphatidylinositol phosphates.

In another exemplary embodiment, the phosphatidylinositol phosphate-binding material may be those which include the pleckstrin homology (PH) domain. The PH domain is a biosensor that binds to intracellular PtdIns(3,4,5)P$_3$ (FIG. 11a, T. Balla, *J Cell Sci* 118, 2093-2104, 2005; Benchun Miaoa et al., *Proc Natl Acad Sci USA*. 2010 Nov. 16; 107 (46):20126-31). In another exemplary embodiment, it was confirmed that a recombinant Akt protein can bind to PtdIns(3,4,5)P$_3$ externalized on the surface of apoptotic cells via PH domain (FIGS. 11b and 11c). Additionally, it was also confirmed that the recombinant PH domain expressed in *E. coli* can detect apoptosis (FIGS. 13 and 14).

As a non-limiting example, the PH domain-containing protein may be selected from the group consisting of Akt (protein kinase B), Btk (Bruton's tyrosine kinase), PDK1 (pyruvate dehydrogenase kinase 1), GRP1 (general receptor of phosphoinositides 1), OSBP (Oxysterol-binding protein 1), ARF (ADP ribosylation factor), IRS1 (Insulin receptor substrate 1), and CERK (ceramide kinase). However, the amino acid sequences of Akt, Btk, PDK1, GRP1, OSBP, ARF, IRS1, and CERK are known in the art and they are known as PH domain-containing proteins. However, any PH domain-containing protein that binds to phosphatidylinositol phosphates can be included without limitation.

In still another exemplary embodiment, the phosphatidylinositol phosphate-binding material may include C2 domain-containing proteins. It may indicate that C2 domain belongs to PKC (protein kinase C) (*Adv Exp Med Biol*. 2012; 740:663-83).

As a non-limiting example, the C2 domain-containing protein may be a PKCβ1 C2 domain protein to which Myc, a transcription factor, is bound (PKCβ1 C2 domain-Myc). The proteins may be those where Myc is directly or indirectly connected to the PKCβ1 C2 domain proteins known in the art. For example, the proteins may be those where PKCβ1 C2 domain proteins and Myc are connected by a linker. Any protein which includes a C2 domain that binds to phosphatidylinositol phosphates may be included without limitation.

For example, the composition for detecting apoptosis containing a C2 domain-containing protein may further contain calcium. Calcium may be contained in an amount of 0.0001 mM to 100 mM, specifically 0.001 mM to 10 mM, more specifically 0.001 mM to 0.5 mM, and even more specifically 0.001 mM to 0.1 mM, based on the total composition (FIGS. 15a and 15b). When calcium is contained in a concentration of the above range, due to the excellent binding affinity of C2 domain-containing proteins to phosphatidylinositol phosphates, and specifically to PI(3,4,5)P$_3$ and PI(4,5)P$_2$, the composition has more excellent effect of detecting apoptosis.

In still another exemplary embodiment, the phosphatidylinositol phosphate-binding material may be those which contain CD14 protein or a variant thereof, a pleckstrin homology (PH) domain-containing protein, a C2 domain-containing protein, and a mixture thereof.

The phosphatidylinositol phosphate-binding material may include anti-PtdIns(3)P antibody, anti-PtdIns(4)P antibody, anti-PtdIns(5) antibody, anti-PtdIns(3,4)P$_2$ antibody, anti-PtdIns (3,5)P$_2$ antibody, anti-PtdIns(4,5)P$_2$ antibody, and anti-PtdIns(3,4,5)P$_3$ antibody. The antibodies can recognize and bind to PtdIns(3)P, PtdIns(4)P, PtdIns(5), PtdIns(3,4)P$_2$, PtdIns(3,5)$P_2$, PtdIns(4,5)$P_2$, or PtdIns(3,4,5)$P_3$, and thus they can be effectively used for the detection of apoptosis.

In an exemplary embodiment, the composition of the present invention may contain calcium; and annexin V as a phosphatidylinositol phosphate-binding material. When treated along with calcium, annexin V binds very strongly to phosphatidylinositol phosphates and thus the composition can detect apoptosis with improved accuracy (FIG. 16).

Calcium may be contained in an amount of 0.1 μM to 100 mM, specifically 1 μM to 100 mM, and more specifically 2.5 μM to 75 mM. When calcium is contained in a concentration of the above range, due to the excellent binding affinity of annexin V to phosphatidylinositol phosphates, and specifically to PI(3,5)$P_2$, PI(4,5)$P_2$, and PI(3,4,5)$P_3$, the composition can have more excellent effect of detecting apoptosis.

The detection of apoptosis may be performed in vitro. For example, the presence and level of apoptosis can be confirmed in cells cultured in vitro using the composition for detecting apoptosis.

The cells may include all the cells in the body.

In the composition for detecting apoptosis, the phosphatidylinositol phosphate-binding material may be labeled with a labeling material. In an exemplary embodiment, the labeling material may be any one selected from the group consisting of fluorescent materials, chromogenic enzymes, radioisotopes, chromophores, superparamagnetic particles, and ultrasuper paramagnetic particles, but is not limited thereto, and any labeling material conventionally used for confirming the presence of a material in the art may be used. The labeling material may bind to a phosphatidylinositol phosphate-binding material and visualize the material. Accordingly, the presence and amounts of the phosphatidylinositol phosphates, which are signals of apoptosis, can be easily confirmed.

The fluorescent materials are materials that exhibit fluorescence and any material used as a fluorescence-labeling material in the art, such as GFP (green fluorescent protein), HRP (horseradish peroxidase), alkaline phosphatase, colloidal gold (coloid gold), FITC (poly L-lysine-fluorescein isothiocyanate), RITC (rhodamine-B-isothiocyanate), Texas-Red, etc., may be used without limitation. The non-limiting examples of the fluorescent materials may include FITC, RITC, alexa 647, APC, fluorescent proteins GFP (green fluorescent protein); EGFP (enhanced green fluorescent protein), RFP (red fluorescent protein); DsRed (Discosoma sp. red fluorescent protein); CFP (cyan fluorescent protein), CGFP (cyan green fluorescent protein), YFP (yellow fluorescent protein)), Cy3, Cy5, or Cy7.5.

A non-limiting embodiment of the chromogenic enzymes may include peroxidase or alkaline phosphatase, but any one used as a chromogenic enzyme in the art may be included without limitation.

A non-limiting embodiment of the radioisotopes may include 125I, 32P, or 35S, but any radioisotope used in the art may be included without limitation.

The chromophores may be, for example, iron ($Fe^{2+}$), which binds to a heme and transports oxygen, or copper ($Cu^+$), which is involved in electron transfer in cell respiration. In addition to the above materials, any material which can visualize the phosphatidylinositol phosphate-binding material may be used as a labeling material without limitation.

Detection methods according to labeling are widely known in the art, but the detection may be performed by the following method. In a case when a fluorescent material is used as a detectable label, an immunofluorescence method may be used. For example, a phosphatidylinositol phosphate-binding material is labeled with a fluorescent material, reacted with a sample, unbound or non-specific binding products are removed therefrom, and the resultant is observed under a fluorescence microscope in the presence of a phosphatidylinositol phosphate, or the fluorescent value thereof may be measured. Additionally, in a case when an enzyme is used as a detectable label, the absorbance may be measured by a color reaction of a substrate via an enzyme reaction, whereas when a radioisotope is used as a detectable label, the detection can be performed by measuring the amount of radiation emission.

In another aspect, the present invention provides a kit for detecting apoptosis including the composition for detecting apoptosis. The composition for detecting apoptosis is the same as described above. Since the composition for detecting apoptosis contains a labeling material which can visualize phosphatidylinositol phosphate-binding materials, the presence and level of apoptosis can be easily detected on a real-time basis.

In still another aspect, the present invention provides a method for detecting apoptosis, including: a first step of treating a cell-containing sample with the composition for detecting apoptosis; and a second step of detecting a labeling material from the sample.

Above all, the first step is a step of treating a cell-containing sample with a composition containing a phosphatidylinositol phosphate-binding material for detecting apoptosis. The method of treating a sample with the composition may be performed using any method used in the art without limitation.

The second step is a step of detecting a labeling material from the sample. The method of detecting the labeling material is the same as described above.

Since the composition for detecting apoptosis contains a labeling material which can visualize phosphatidylinositol phosphate-binding materials, which are apoptosis signals, the presence and level of apoptosis can be easily detected on a real-time basis.

A Composition for Screening Anticancer Agents and a Method for Screening

In still another aspect, the present invention provides a composition for screening anticancer agents, containing a composition for detecting apoptosis. The composition for detecting apoptosis is the same as described above.

The present inventors have confirmed that phosphatidylinositol phosphates can act as signals of apoptotic cells, and in this regard, they have first identified that anticancer agents capable of inducing apoptosis of cancer cells can be screened by detecting phosphatidylinositol phosphates.

The cancer cells may include all kinds of cancer cells that may occur in the body, such as oral cavity cancer, lung cancer, kidney cancer, cardiac cancer, skin cancer, breast cancer, etc.

The anticancer agent refers to a material which can induce or promote apoptosis of cancer cells, and in the specification of the present invention, it may be used as the same meaning as a cytotoxic agent or apoptosis-inducing agent. For example, the anticancer agent may be an alkylating agent or topoisomerase inhibitor, but is not limited thereto as long as it is used as a cytotoxic agent.

The alkylating agent may be one selected from the group consisting of cisplatin, carboplatin, oxaliplatin, Nedaplatin, Satraplatin, triplatin tetranitrate, cyclophosphamide, mechlorethamine, uramustine, melphalan, chlorambucil, ifosfamide, carmustine, lomustine, streptozocin, and Busulfan.

Additionally, the topoisomerase inhibitor may be one selected from the group consisting of irinotecan, topotecan, amsacrine, etoposide phosphate, doxorubicin, mitoxantrone, ellipticine, aurintricarboxylic acid, HU-331, epipodophyllotoxin, teniposide, camptothecin, cycloheximide, dexamethasone, and etoposide.

In still another aspect, the present invention provides a method for screening anticancer agents, which includes: a first step of treating a cancer cell-containing sample with the composition for screening anticancer agents and a candidate material thereof; and a second step of detecting a labeling material from the sample. The method may further include a third step, where the candidate material is determined as an anticancer agent when a labeling material is detected from the sample.

The first step relates to treatment of a cancer cell-containing sample with the composition for screening anticancer agents and the candidate material. The candidate material may refer to any material suspected as an anticancer agent. As the treatment method for use, any method widely used in the art may be used without limitation.

The second step relates to detection of a labeling material contained in the composition for screening, from the treated sample. The method for detecting the labeling material is the same as described above.

Since the composition for screening contains a labeling material which can detect phosphatidylinositol phosphates that are externalized during apoptosis, the presence and level of apoptosis by an anticancer agent can be easily detected on a real-time basis. Accordingly, when phosphatidylinositol phosphates are detected by a labeling material, the candidate material may be determined as an anticancer agent.

A Composition for Screening Apoptosis-Inhibiting Materials and a Screening Method Thereof In still another aspect, the present invention provides a composition for screening apoptosis-inhibiting materials, containing a composition for detecting apoptosis. The composition for detecting apoptosis is the same as described above.

In still another aspect, the present invention provides a method for screening apoptosis-inhibiting materials, which includes: a first step of treating a cell-containing sample with the composition for detecting apoptosis and the candidate material; a second step of inducing apoptosis; and a third step of quantifying a labeling material from the sample. The method may further include a fourth step, wherein when the amount of the labeling material detected from the sample in the third step is smaller than that of the labeling material detected from the sample, in which apoptosis was induced without treating with a candidate material, the candidate material is determined as an apoptosis-inhibiting material.

First, the first step relates to treating a cell-containing sample with the composition for detecting apoptosis and the candidate material. The candidate material may refer to any material suspected as an apoptosis-inhibiting material. As the treatment method for use, any method widely used in the art may be used without limitation.

The second step relates to induction of apoptosis of cells contained in the sample. As the method of inducing apoptosis, any method generally used for apoptosis in the art may be used without limitation. For example, cells may be cultured in a condition where apoptosis can be induced. Alternatively, for example, the apoptosis of the cells contained in the sample may be induced by treating the cells with an apoptosis-inducing agent. The apoptosis-inducing agent may be an anticancer agent. In an exemplary embodiment of the present invention, camptothecin, cycloheximide, dexamethasone, and etoposide were used as the apoptosis-inducing agent. Dexamethasone may be used in a concentration of 15 µM to 25 µM, camptothecin in a concentration of 2 µM to 5 µM, etoposide in a concentration of 80 µM to 120 µM, and cycloheximide in a concentration of 150 µM to 250 µM, but the concentration of the apoptosis-inducing agent is not limited thereto.

In the second step, the apoptosis-inducing agent may be treated for 1 hour to 10 hours, and preferably, 2 hours to 8 hours. When the apoptosis-inducing agent is treated for the above length of time, phosphatidylinositol phosphates can be detected more effectively (FIGS. 3a and 3b).

The third step is a step of quantifying a labeling material from the sample. As the method for quantification, any method for quantifying labeling materials such as fluorescent materials, chromogenic enzymes, radioisotopes, chromophores, superparamagnetic particles, and ultrasuper paramagnetic particles used in the art may be used without limitation. For example, when a fluorescent material is used as a detectable label, immunofluorescence method may be used. For example, a phosphatidylinositol phosphate-binding material is labeled with a fluorescent material, reacted with a sample, and unbound or non-specific binding products are removed therefrom, and then, under a fluorescent microscope, the fluorescence value according to the presence of phosphatidylinositol phosphates can be measured. Additionally, when an enzyme is used as a detectable label, the absorbance can be measured by a color reaction of a substrate via an enzyme reaction, whereas when a radioisotope is used as a detectable label, the detection can be performed by measuring the amount of radiation.

The fourth step is a step, where when the amount of the labeling material detected from the sample in the third step is smaller than that of the labeling material detected from the sample, in which apoptosis was induced without treating with a candidate material, the candidate material is determined as an apoptosis-inhibiting material. When the phosphatidylinositol phosphates, which act as signals of apoptotic cells, are detected in a smaller amount in a sample treated with a candidate material, compared to that detected in a sample not treated with the candidate material, the candidate material may be determined to inhibit apoptosis.

A Composition for Inhibiting Phagocytosis and an Inhibitory Method Thereof

In still another aspect, the present invention provides a composition for inhibiting phagocytosis, containing a phosphatidylinositol phosphate-binding material.

In an exemplary embodiment of the present invention, it was confirmed that phosphatidylinositol phosphates act as signals of apoptotic cells and phagocytosis is induced as a result. When phosphatidylinositol phosphates which are externalized upon apoptosis are capped, phagocytosis may be inhibited. Accordingly, the composition for inhibiting phagocytosis can inhibit unnecessary phagocytosis and thereby exhibit a cytoprotective effect.

The phosphatidylinositol phosphates may be phosphatidylinositol-3-phosphate (PtdIns(3)P), phosphatidylinositol-4-phosphate (PtdIns(4)P), phosphatidylinositol-5-phosphate (PtdIns(5)P), phosphatidylinositol-3,4-biphosphate (PtdIns(3,4)P$_2$), phosphatidylinositol-3,5-biphosphate (PtdIns(3,5)P$_2$), phosphatidylinositol-4,5-biphosphate (PtdIns(4,5)P$_2$), or phosphatidylinositol-3,4,5-triphosphate (PtdIns(3,4,5)P$_3$), and these are the same as described above.

The phosphatidylinositol phosphate-binding material may be CD14 protein or a variant thereof, a protein including a pleckstrin homology (PH) domain, a protein including the C2 domain of PKC (protein kinase C), an anti-PtdIns(3)P antibody, an anti-PtdIns(4)P antibody, an anti-PtdIns(5) antibody, an anti-PtdIns(3,4)$P_2$ antibody, an anti-PtdIns(3,5)$P_2$ antibody, an anti-PtdIns(4,5)$P_2$ antibody, or an anti-PtdIns(3,4,5)$P_3$, and a mixture thereof, and these are the same as described above.

The composition may contain calcium; and annexin V as a phosphatidylinositol phosphate-binding material. The combined treatment of annexin V and calcium can significantly increase the binding affinity and thus phagocytosis can be effectively inhibited. Calcium may be contained in an amount of 0.1 μM to 100 mM, preferably 1 μM to 100 mM, and more preferably 2.5 μM to 75 mM, relative to the total composition. When calcium is contained in a concentration of the above range, due to the excellent binding affinity of annexin V to phosphatidylinositol phosphates, and specifically to PI(3,5)$P_2$, PI(4,5)$P_2$, and PI(3,4,5)$P_3$, the composition can have more excellent effect of inhibiting phagocytosis.

The composition for inhibiting phagocytosis may be treated in cells, tissues, or organs for transplantation. For example, the cell for transplantation may be a pancreatic islet cell. For example, the tissue for transplantation may be a pancreatic tissue. For example, the organ for transplantation may be the pancreas.

Apoptosis may be induced during the various steps in isolating cells-, tissues-, or organs for transplantation. Accordingly, the composition for inhibiting phagocytosis may be treated when cells, tissues, or organs for transplantation are isolated. The apoptosis and subsequent phagocytosis during the isolation and ablation of cells, tissues, or organs for transplantation may be inhibited by capping by the composition for inhibiting phagocytosis, thereby increasing the survival rate of cells, tissues, etc. (FIG. 1a).

In another exemplary embodiment, the composition may be treated during the storage process of the isolated or ablated cells, tissues, or organs. The capping by the composition for inhibiting phagocytosis can also inhibit unnecessary phagocytosis thereby protecting cells and reducing the side-effects of transplantation. However, the method for treating the composition is not limited thereto, but any method which is used to treat phagocytosis-inhibiting materials in the art may be used as a method for treating the composition, without limitation.

In still another aspect, the present invention provides a method for inhibiting phagocytosis, including treating the composition for inhibiting phagocytosis in cells, tissues, or organs. The pre-treatment of the composition for inhibiting phagocytosis in cells, tissues, or organs can inhibit unnecessary phagocytosis and thereby protect cells and reduce the side-effects of transplantation. As the treatment method, any method that is widely used in the art may be used without limitation.

The treatment step may be performed outside the body of an individual. For example, the side-effects of transplantation (e.g., graft-versus-host reactions) can be prevented, by treating the composition for inhibiting phagocytosis in cells, tissues, or organs which are isolated, cultured after isolation, or separately prepared from a first individual, followed by transplantation of the cells, tissues, or organs into a second individual. Accordingly, the method for inhibiting phagocytosis according to the present invention can be used for the treatment of transplantation-related immune diseases.

DETAILED DESCRIPTION OF THE INVENTION

Hereinafter, the present invention will be described in more detail with reference to the following Examples. However, these Examples are for illustrative purposes only, and the invention is not intended to be limited by these Examples.

Example 1. Confirmation of the Effect of Detecting Apoptosis by Phosphatidylinositol Phosphates (PtdInsPs)

1-1. Induction of Apoptosis

Specifically, HeLa cells, Jurkat T cells, and Chinese hamster ovary (CHO) K1 cells were cultured in DMEM-, RPMI-, and F12 media containing 10% FBS and 1% penicillin/streptomycin, respectively. Then, the cells were cultured on the cover glass in a 6-well plate at a density of $1 \times 10^5$ cells/mL for 24 hours and treated with an apoptosis-inducing kit (ab102480; Abcam, Cambridge, Mass., USA) at 37° C. for 6 hours, and specifically, treated with 4 μM camptothecin, 200 μM cycloheximide, 20 μM dexamethasone, and 100 μM etoposide.

1-2. Observation of Phosphatidylinositol Phosphates in Apoptotic Cells

To confirm whether phosphatidylinositol phosphates appear on the surface of cells where apoptosis was induced, the cells in which apoptosis was induced in Example 1-1 was fixed with formalin (10% neutral buffered) for 5 minutes and washed twice with PBS. Then, the cells were treated with a serum-free protein blocking solution (Dako) along with monoclonal mouse IgM anti-PtdIns(4,5)$P_2$ or anti-PtdIns(3,4,5)$P_3$ antibody (1:100, Echelon Biosciences, Salt Lake City, Utah, USA) for 30 minutes, and treated with FITC-labeled donkey anti-mouse IgM secondary antibody for 30 minutes.

Then, the cells were placed on a microscope and photographed by the Zeiss LSM 710 laser-scanning confocal microscope (Carl Zeiss) with appropriate excitation using a release filter set. The images were photographed using 40× oil immersion lens. The fluorescence intensity of the unprocessed original images was quantified using ZEN 2010 software (Carl Zeiss).

As a result, externalized PtdIns(3,4,5)$P_3$ was observed on the surface of apoptotic cells at the early stage of apoptosis (FIG. 2a) and the secondary necrosis (FIG. 2b). The externalization appeared regardless of the kinds of apoptosis-inducing agents or the kinds of cells (FIG. 2c). Accordingly, it was confirmed that the induction of apoptosis into cells results in the externalization of phosphatidylinositol phosphates in the outer layer of the plasma membrane and the apoptosis can be detected by observing the phosphatidylinositol phosphates.

It was also confirmed that PtdIns(4,5)$P_2$ were also externalized in the final stage of apoptosis when they were stained with propidium iodide (FIG. 2d) thus enabling the detection of apoptosis.

Example 2. Detection of Phosphatidylinositol Phosphate-Binding Materials 2-1. Isolation of PtdIns(3,4,5)$P_3$ For the detection of materials capable of detecting phosphatidylinositol phosphates, PtdIns(3,4,5)$P_3$ were isolated from the cells where apoptosis was induced as described below.

Jurkat T cells or HeLa cells were cultured in plates (100 cm$^3$) in a concentration of $1 \times 10^7$ cells/mL for 16 hours. Then, the cells were treated with 10 μM dexamethasone, 4 μM camptothecin, or 100 μM cycloheximide at various time-points (0-, 1-, 2-, 4-, 6-, 8-, 18-, and 24-hour) to induce apoptosis, and the cells were recovered and acidic lipids were extracted therefrom using the method described below according to the manual of the manufacturer (Echelon Biosciences).

First, the cells were washed with 10 mL of cold 0.5 M trichloroacetic acid (TCA) and the cells attached to a flask were recovered and centrifuged at 1,500 rpm for 5 minutes. The cell pellet was washed twice with 5% TCA (3 mL) containing 1 mM EDTA solution, and 2.25 mL of a mixture of MeOH/CHCl$_3$:12 M HCl (80:40:1, v/v) was added thereto and vortexed 4 times at room temperature for 15 minutes. Then, the resultant was centrifuged at 15,000 rpm for 5 minutes. The supernatant was recovered and CHCl$_3$ (0.75 mL) and 0.1 M HCl (1.35 mL) were added thereto to isolate acidic lipids, and the resulting organic phase was dried in a vacuum dryer and stored at −80° C. (long-term storage) or 4° C. (an immediate use for experiments) according to its use.

Then, the concentration of PdtIns(3,4,5)P$_3$ was measured by enzyme-linked immunosorbent assay (ELISA; K-2500s, Echelon Biosciences) using biotinyl-monoclonal IgG anti-PtdIns(3,4,5)P$_3$ antibody and streptavidin-horseradish peroxidase, and the production of PdtIns(3,4,5)P$_3$ was confirmed (FIGS. 3a and 3b). FIG. 3a shows the concentrations of PdtIns(3,4,5)P$_3$ isolated from Jurkat T cells according to time and treating materials and FIG. 3b shows the concentrations of PdtIns(3,4,5)P$_3$ isolated from HeLa cells according to time and treating materials.

2-2. Preparation of Recombinant CD14 Proteins and Variants Thereof

The recombinant CD14 proteins were produced by the method described below: first, human wild-type CD14 cDNA encoding the entire length of CD14 (1$^{st}$ to 365$^{th}$ residues) was amplified by PCR using the following primers (Genemed Synthesis, Inc.).

```
Forward Primer
                                   -SEQ ID NO: 1
5'-TTGGTGCCAACAGATGAGGTTCAC-3'

Reverse Primer
                                   -SEQ ID NO: 2
5'-TTCTTTCCTACACAGCGGCACCC-3'
```

Then, a protein having V5 and His6 tags at the C-terminus was produced by replicating into the HindIII and XbaI restriction sites of pcDNA6 V5 HisA (Invitrogen) using the QuikChange Site-Directed Mutagenesis Kit (Invitrogen) and the protein was confirmed by sequence analysis. Then, the above linear vector (10 μg) was transfected into CHO K1 cells using Lipofectamine Plus reagent according to the manufacturer's manual. Two days after the transfection, the CHO K1 cells were treated with blasticidin (5 μg/mL) every two days and thereby a blasticidin-resistant stable cell line was obtained. An immunoblotting was performed with anti-CD14 antibody and the CHO K1-CD14 cells were cultured in F12 medium containing blasticidin (1 μg/mL). Each stable cell line was cultured in 20 plates (150 cm$^3$) for 3 days. Then, the recovered cells were suspended in a lysis buffer (50 mM Tris pH 7.6, 500 mM NaCl, 20 mM imidazole, EDTA-free protease inhibitor cocktail (Roche, Germany)) and sonicated. Then, the purified recombinant proteins were loaded into Ni-NTA agarose resin (Qiagen) and purified by eluting with 50 mM Tris (pH 7.6), 250 mM NaCl, and 300 mM imidazole. Then, the purified recombinant proteins were dialyzed with 50 mM Tris (pH 7.6) and 20 mM NaCl and further purified by gel filtration (Superdex-200 FPLC) chromatography and thereby recombinant CD14 receptor proteins were obtained.

Quadruple mutant CD14 receptor proteins (which block PtdIns(3,4,5)P$_3$) were prepared in the same manner.

2-3. Confirmation of a Binding Between CD14 Protein and a Phosphatidylinositol Phosphate: Protein-Lipid Overlay Assay and Immunoblotting To confirm whether the inositol phosphpate groups of various phosphatidylinositol phosphates directly bind to macrophage CD14 receptors, a protein-lipid overlay assay was performed using the full-length recombinant human CD14 proteins and variant CD14 proteins prepared in Example 2-2. PIP strips or PIP arrays were purchased from Echelon Biosciences.

After culturing a cell membrane for 15 minutes, non-specific bindings to the cell membrane was blocked using TBS-T (50 mM Tris, 0.15 M NaCl, and 0.05% Tween-20, pH 7.4, EDTA-free protease inhibitor cocktail; Roche, Germany) containing 3% BSA. After the blocking, the cell membrane was incubated along with each of the purified recombinant CD14 proteins (100 pmol) for 30 minutes, washed 3 times with PBS, incubated again with anti-CD14 (rabbit, HPA002127; Sigma-Aldrich), and incubated with horseradish peroxidase (HRP)-labeled secondary antibody (goat; HAF007; R&D Systems) for 30 minutes. The binding was detected using the ImageQuant LAS 4000 (Fujifilm, Japan). As described in Toda et al. (Mol Cell Biol 32, 118, 2012), PIP-affinity bead pulldowns were performed.

Then, the purified wild-type or variant proteins were subjected to a 4-fold dilution according to the concentration of each protein, transferred into 30 μL of TBS-T containing phosphoinositol beads (40 μL) and 20 mM IC-InsP$_6$ (Iron-Calcium-InsP$_6$ (phytate)) and gently mixed for 30 minutes. The settled beads were washed 4 times with TBS-T. The proteins were eluted with SDS sample buffer, separated by SDS-PAGE, and detected by immunoblotting (anti-CD14 antibody; HPA002127; Sigma).

As a result, it was confirmed that CD14 showed strong binding affinities for various phosphatidylinositol phosphates but showed no binding affinity for phosphatidylserine, phosphatidylcholine, and sphingosine-1-phosphate (FIG. 4a).

Additionally, as a result of immunoblotting, it was confirmed that CD14 showed the strongest binding with PtdIns (3,4,5)P$_3$ at the strength of 6.3 pmol (FIG. 4b). This result suggests that CD14 receptors directly bind to phosphatidylinositol phosphates by an inositol phosphpate group.

Additionally, as a result of PIP-affinity bead pulldowns, it was confirmed that when CD14 is a modified protein, it cannot bind to PIP beads, whereas a wild-type CD14 protein can bind to PtdIns(3)P, PtdIns(4)P, PtdIns(5)P, PtdIns(4,5)P$_2$, and PtdIns(3,4,5)P$_3$ (FIG. 4c).

Example 3 Confirmation of the Effect of Detecting Apoptosis by a Specific Binding of CD14 Protein to PtdInsPs 3-1. Preparation of IC-InsP$_6$ As PtdInsPs consist of myo-inositol phosphates such as Ins(1,4,5)P$_3$ and Ins(1,3,4,5)P$_4$, and InsP$_6$ acts by mimicking PtdInsPs. Accordingly, experiments were performed as described below using InsP$_6$.

Meanwhile, since ferric ions are stained by Prussian blue, irons were bound to InsP$_6$ for easy monitoring of the intracellular location of InsP$_6$ (Fe$^{3+}$-InsP$_6$). Specifically, 10 mM Fe$^{3+}$-InsP$_6$ solution was prepared by mixing an equimolar concentration of Fe$^{3+}$ ions and InsP$_6$ (phytate, hexakisphosphate) solution (pH 6.0). Then, to minimize the possibility for the $Fe^{3+}$-$InsP_6$ to chelate calcium in the blood, an equimolar concentration of $Ca^{2+}$ ions was added to the $Fe^{3+}$-$InsP_6$ solution. Then, an IC-$InsP_6$ ($Fe^{3+}$—$Ca^{2+}$-$InsP_6$) solution, whose pH was adjusted to 6.0 by adding 1 N NaOH, was prepared. FIG. 5 shows the chemical structure of IC-$InsP_6$.

3-2. Evaluation of IC-$InsP_6$ Absorption by Peritoneal Macrophages

Animal experiments were approved by the Institutional Animal Care and Use Committee and all the animals for use were handled according to the ethics guidelines and the safety guidelines for genetic manipulation experiments for animal experiments in Gachon University Lee Gil Ya Cancer and Diabetes Institute.

Thioglycollate-elicited peritoneal macrophages (Thio-pMacs) in a C57BL/6 mouse were obtained. Specifically, 2 mL of 3% Brewer thioglycollate medium (Difco, Detroit, Mich., USA) was intraperitoneally injected the mouse, and 3 to 5 days thereafter, the peritoneum of the mouse was washed with cold PBS to recover peritoneal macrophages. The cells were centrifuged at 1,500 rpm for 5 minutes. The resulting pellet was washed 3 times with PBS, resuspended in DMEM medium containing 10% FBS (Gibco), and cultured on the cover glass in a 6-well plate (Nunc, Fisher Scientific) at a density of $1\times10^5$ cells/mL. The cells were cultured by adhesion culture, and the slides were washed to remove the suspending cells. Then, the adhered Thio-pMacs cells were cultured according to the presence of LPS (0.5 µg/mL) for 6 hours. LPS induces the activation of Thio-pMacs.

After cultivation, the cells were treated with IC-$InsP_6$ (0 mM to 0.5 mM) for 4 hours. The cells were washed with PBS to remove free IC-$InsP_6$, fixed with formalin (10% neutral buffered) for 5 minutes, and stained as described below for the confirmation of intracellular iron absorption. Specifically, the cover glass was placed in a staining solution (5% potassium ferrocyanide and 12% HCl) for 1 hour, washed 3 times with distilled water, and stained with Prussian blue. Then, the resultant was counterstained with nuclear fast red and placed in a mounting medium (Thermoscientific, Somerset, N.J., USA).

As a result, it was confirmed that the activated Thio-pMacs by LPS stimulation showed an effective phagocytosis of IC-InsP6 compared to non-activated Thio-pMacs and that this effect was increased in a treatment concentration-dependent manner (FIG. 6a).

Meanwhile, as a result of the same experiment, it was confirmed that RAW264.7 macrophages also showed an effective phagocytosis of IC-$InsP_6$ in a treatment concentration-dependent manner (FIGS. 6b and 6c). These results suggest that IC-$InsP_6$ is subjected to selective phagocytosis by activated macrophages.

3-3. Molecular Modeling and Sequence Alignment

To confirm the residues of $InsP_6$ that bind to CD14 receptors, molecular modeling was performed as described below.

First, the coordinate of highly purified InsP6 was docketed into CD14 (PDBid: 1WWL) crystalline structure in hADAR2 (PDBid: 1ZY7) using AutoDock PyRx (pyrx-.sourceforge.net/). During the docketing, InsP6 was treated to recognize CD14 as a receptor and the flexibility of a rotatable binding of CD14 was maintained while maintaining its rigidity. The grid box was covered in x, y, and z directions of the total CD14 protein. The ten conformations having the minimum energy reported by AutoDock PyRx were confirmed using the PyMOL software (www.pymol.org). Among the ten minimum energy conformations, the first molecule (−6.2 kcal/mol, binding affinity) was selected without confirming the root-mean-square deviation (RMSD) value to proceed with a further experiment. All computer calculations were performed using the disclosed CD14 structure (PDBid: 1WWL) (J. I. Kim et al., *J Biol Chem*, 280, 11347-11351, 2005). The five sequences (cows, rabbits, humans, mice, and rats) corresponding to CD14 family were all downloaded from SwissProt and aligned with ClustalW.

As a result, it was confirmed that the 1-, 3-, 4-, 5-phosphate groups of $InsP_6$ or $PtdIns(3,4,5)P_3$ are fixed by R93, R148, R150, and R230 amino acid residues and salt bridges (FIG. 7a). These results can explain why recombinant CD14 showed the highest binding affinity to $PtdIns(3,4,5)P_3$ in the protein-lipid overlay experiment (FIG. 3b). The sequence alignment based on structures confirms that these amino acid residues are well conserved among species (FIG. 7b). Since acidic inositol phosphate groups are essential for binding to basic amino acid residues of proteins, it was confirmed that the basic residues, such as R93, R148, R150, and R230, in CD14 can mediate protein-lipid bindings.

3-4. Confirmation of Interactions Between CD14 Proteins and Apoptotic Cells

To confirm whether CD14 protein can directly recognize the $PtdIns(3,4,5)P_3$ exposed to apoptotic cells, an experiment was performed as described below.

First, HeLa and CHO cells were treated with 4 µM camptothecin for 6 hours to induce apoptosis, fixed with formalin (10% neutral buffered) for 5 minutes, and washed twice with PBS. Then, the cells were treated with a serum-free protein blocking solution (DAKO) and cultured with 2 µg purified recombinant wild-type (WT) CD14 and quadruple mutant CD14 receptor proteins (which block PtdIns(3,4,5)$P_3$) for 30 minutes. Then, the HeLa and CHO cells, which were bound to the wild-type CD14 and quadruple variant CD14 proteins, were treated with rabbit anti-CD14 antibody (HPA00212; 1:200, Sigma-Aldrich USA) or the pleckstrin homology (PH) domain of monoclonal mouse anti-Akt1 antibody (05-591, 1:100, Millipore) for 30 minutes, and treated with FITC-labeled secondary antibody for 30 minutes. Then, the resultant was counterstained with DAPI to visualize nuclei, and counterstained with propidium iodide to distinguish apoptotic cells.

Then, the cells were placed on a differential interference contrast (DIC) microscope and photographed by the Zeiss LSM 710 laser-scanning confocal microscope (Carl Zeiss) with appropriate excitation using a release filter set. The images were photographed using 40× oil immersion lens. The fluorescence intensity of the unprocessed original images was quantified using ZEN 2010 software (Carl Zeiss).

As a result, as illustrated in FIG. 8, it was confirmed that the wild-type recombinant CD14 receptors were immediately bound to the surfaces of apoptotic cells, whereas the CD14 receptors, which were modified to block the binding of $PtdIns(3,4,5)P_3$, did not recognize apoptotic cells. These results suggest that CD14 can directly bind to externalized $PtdIns(3,4,5)P_3$ in apoptotic cells and thereby recognize apoptotic cells and act as a signal for phagocytosis.

3-5. Loss of Binding Affinity of CD14−/− Mouse Macrophages to $PtdIns(3,4,5)P_3$ (1) Evaluation of Phagocytosis of Liver Kupffer Cells CD14-defective ($CD14^{-/-}$) C57BL/6 mice purchased from Jackson Laboratory USA were intra-arterially injected with IC-$InsP_6$, livers were isolated from the mice, and the phagocytosis with respect to IC-InsP$_6$ was confirmed via immunohistochemistry and Prussian blue staining, as described below.

First, liver tissues were respectively isolated from the CD14-defective C57BL/6 mice (n=5 per group), fixed with formalin (10% neutral buffered), and placed in paraffin. Then, the liver tissues were boiled in Tris/EDTA (pH 9.0) in a microwave for 2 minutes and antigens were recovered therefrom. For detecting IC-InsP$_6$ in cytoplasmic macrophages, the liver tissues were incubated with mouse monoclonal anti-F4/80 (Bm8, 1:100; eBioscience, San Diego, Calif., USA) at room temperature for 90 minutes. Then, the liver tissues were incubated along with a secondary antibody, to which horseradish peroxidase was bound, for 30 minutes, and the presence of IC-InsP$_6$ was detected using 3,3'-diamino-benzidine tetrahydrochloride (Dako, Glostrup, Denmark). Then, the resultant was stained with Prussian blue. The Kupffer cells were confirmed with F4/80 antibody and phagocytosis was confirmed by Prussian staining.

As a result, it was confirmed that the CD14-defective Kupffer cells in the liver of the mice hardly phagocytized IC-InsP$_6$, whereas the wild-type Kupffer cells in the liver effectively phagocytized IC-InsP$_6$ (FIG. 9a). These results suggest that the CD14 of macrophages can directly control the phagocytosis of IC-InsP$_6$ which mimics PtdIns(3,4,5)P$_3$.

(2) In Vitro Phagocytosis Assay

To confirm whether the externalization of PdtIns(3,4,5)P$_3$ is essential for the CD14-mediated phagocytosis, after activating the macrophages which were isolated from wild type or CD14 defective mice by LPS treatment, the PHrodo-labeled apoptotic Jurkat T cells were subjected to an in vitro phagocytosis assay. In particular, the treatment of anti-PdtIns (3,4,5)P$_3$ antibody was varied.

First, Jurkat T cells were cultured overnight in a concentration of 5×10$^6$ cells/mL and treated with dexamethasone (20 μg/mL) for 6 hours. The grown or apoptotic Jurkat T cells were washed with PBS and cultured with pHrodo Red AM (P353721, Life Technologies, USA) at room temperature for 30 minutes. The PHrodo-labeled apoptotic Jurkat T cells were washed with a live cell imaging solution (A14291DJ, Life Technologies, USA).

Meanwhile, Thio-pMacs were cultured in a 6-well plate in a concentration of 5×10$^6$ cells/mL for 16 hours and treated with LPS (0.5 μg/mL) for 6 hours.

Then, the PHrodo-labeled apoptotic Jurkat T cells were treated with Thio-pMacs activated by LPS for 2.5 hours. After the cultivation, the plate was washed with PBS to remove the PHrodo-labeled apoptotic Jurkat T cells, fixed with formalin (10% neutral buffered) for 5 minutes, and counterstained with DAPI to visualize nuclei. The degree of phagocytosis was observed under a confocal microscope as described in Examples above.

As a result, as illustrated in FIG. 9b and FIG. 9c, which illustrates the quantified result of FIG. 9b, it was confirmed that the activated macrophages (LPS-stimulated Thio-pMacs), isolated from the CD14-defective mouse, hardly phagocytized the PHrodo-labeled apoptotic cells (Jurkat T cells) compared to the wild-type macrophages. Additionally, the inhibition of the externalization of PdtIns(3,4,5)P$_3$ by the treatment with anti-PdtIns(3,4,5)P$_3$ antibody resulted in the inhibition of the phagocytosis.

That is, as illustrated in FIG. 10, these results suggest that CD14 can recognize apoptosis through a specific binding with PdtIns(3,4,5)P$_3$ and induce phagocytosis with respect to apoptotic cells.

Example 4 Confirmation of Detecting Apoptosis in the PH Domain of Akt Proteins

The PH domain of Akt proteins is a biosensor that binds to intracellular PtdIns(3,4,5)P$_3$ (FIG. 11a, T. Balla, J Cell Sci 118, 2093-2104, 2005). Accordingly, an experiment to confirm whether a PH domain-containing protein can detect apoptosis using the same was performed.

First, HeLa and CHO cells were treated with 4 μM camptothecin for 6 hours to induce apoptosis, fixed with formalin (10% neutral buffered) for 5 minutes, and washed twice with PBS. Then, the cells were treated with the serum-free protein blocking solution (Dako), and cultured along with 2 μg of recombinant Akt proteins (Millipore) for 30 minutes. Then, the HeLa and CHO cells, which were bound to Akt proteins, were treated with rabbit anti-CD14 antibody (HPA00212; 1:200, Sigma-Aldrich USA) or the anti-Akt pleckstrin homology (PH) domain antibody of monoclonal mouse (05-591, 1:100, Millipore) for 30 minutes, and treated with FITC-labeled secondary antibody for 30 minutes. Then, the resultant was counterstained with DAPI to visualize nuclei, and counterstained with propidium iodide to distinguish apoptotic cells.

Then, the cells were placed on a microscope and photographed by the Zeiss LSM 710 laser-scanning confocal microscope (Carl Zeiss) with appropriate excitation using a release filter set. The images were photographed using 40× oil immersion lens. The fluorescence intensity of the unprocessed original images was quantified using ZEN 2010 software (Carl Zeiss).

As a result, it was confirmed that the recombinant Akt protein binds to PtdIns(3,4,5)P$_3$ externalized on the surface of apoptotic cells through a PH domain thereby recognizing apoptosis (FIGS. 11b and 11c).

Example 5 Confirmation of Detecting Apoptosis in a Recombinant PH Domain 5-1. Preparation of a Recombinant PH Domain As illustrated in FIG. 12a, a human Akt PH domain (1$^{st}$ to 144$^{th}$ amino acids) was cloned into pET28a. After expressing the cloned human Akt PH domain in E. coli, it was purified by Ni-NTA column and gel permeation chromatography to prepare a recombinant PH domain.

As illustrated in FIG. 12b, the size of the prepared protein was 21 kDa, thus confirming that it is a PH domain.

In the same manner, human annexin V (1$^{st}$ to 319$^{th}$ amino acids) was cloned into pET28a, expressed in E. coli, and purified to prepare a recombinant annexin V. The size of the protein prepared in FIG. 12c was 37 kDa thus confirming that it is annexin V.

5-2. Confirmation of Detecting Apoptosis in a Recombinant PH Domain

First, apoptosis was induced in CHO cells by treating them with 4 μM camptothecin for 6 hours, and the cells were fixed with formalin (10% neutral buffered) for 5 minutes and washed twice with PBS. Then, the cells were treated with a serum-free protein blocking solution (DAKO) along with the recombinant PH domain prepared in Example 5-1 for 30 minutes. Then, the cells were treated with the anti-Akt PH domain antibody of monoclonal mouse (05-591, 1:100, Millipore) and then treated with FITC-labeled secondary antibody for 30 minutes. Then, the cells were washed with PBS, fixed with formalin (10% neutral buffered) for 5 minutes, and stained. The cells were counterstained with propidium iodide to distinguish apoptotic cells.

The recombinant annexin V prepared in Example 5-1 was subjected to an experiment in the same manner and analyzed by FACS.

Then, the cells were placed on a microscope and photographed by the Zeiss LSM 710 laser-scanning confocal microscope (Carl Zeiss) with appropriate excitation using a release filter set. The images were photographed using 40× oil immersion lens. The fluorescence intensity of the unprocessed original images was quantified using ZEN 2010 software (Carl Zeiss).

As a result, it was confirmed that the PH domain and annexin V bind at different locations from each other on the surfaces of apoptotic cells and that the externalized PtdIns(3,4,5)$P_3$, to which the PH domain binds, and PdtSer, to which the annexin V binds, were simultaneously detected on the surfaces of the apoptosis-induced cells (FIG. 13).

Additionally, as a result of the flow cytometer analysis of the apoptosis, it was confirmed that PdtSer, to which the annexin V binds, was simultaneously detected in the apoptotic cells, in which the recombinant Akt PH domain or recombinant CD14 protein that binds to PtdIns(3,4,5)$P_3$ appeared (FIG. 14).

Example 6 Confirmation of the Binding of C2 Domain Proteins and Phosphatidylinositol Phosphates: a Protein-Lipid Overlay Assay and Immunoblotting To confirm whether the PKCβ1 C2 domain-Myc protein and the inositol phosphpate group in various phosphatidylinositol phosphates directly bind to each other, protein-lipid overlay assay and immunoblotting were performed in the same manner as in Example 2-3. The PIP strip or PIP array was purchased from Echelon Biosciences.

As a result, it was confirmed that the PKCβ1 C2 domain protein exhibited a strong binding affinity for various phosphatidylinositol phosphates even at 100 pmol, but the protein exhibited no binding affinity for phosphatidylserine, phosphatidylcholine, and sphingosine-1-phosphate (left of FIG. 15a).

Additionally, it was confirmed that C2 domain protein was bound to phosphatidylinositol phosphates in a calcium-dependent manner (right of FIG. 15a). The results are shown on the right of FIG. 15b after statistical analysis of the same. In particular, the binding rate reached almost 100% in a concentration of 0.01 mM to 0.25 mM.

Example 7 Confirmation of Calcium-Dependent Binding of Annexin V

Annexin V, which is known to specifically bind to phosphatidylserine, was subjected to protein-lipid overlay assay and immunoblotting in the same manner as in Example 2-3.

As shown on the left of FIG. 16, when the experiment was performed by mixing annexin V with 5 mM EDTA, the binding with phosphatidylinositol phosphates was not shown.

However, as illustrated on the right of FIG. 16, when the experiment was performed by mixing annexin V with 5 μM $CaCl_2$, annexin V was shown to bind to various kinds of phosphatidylinositol phosphates even in its concentration of 100 pmol. Specifically, annexin V showed the strongest bindings to PI(3,5)$P_2$, PI(4,5)$P_2$, and PI(3,4,5)$P_3$, and annexin V was also shown to bind to PI(5)P, PI(3)P, and PI(4)P, as well as to PI(3,4)$P_2$. However, annexin V did not bind to phosphatidylserine.

As described above, annexin V can very strongly bind to phosphatidylinositol phosphates when treated along with calcium, and thus it can detect apoptosis with very high accuracy.

From the foregoing, a skilled person in the art to which the present invention pertains will be able to understand that the present invention may be embodied in other specific forms without modifying the technical concepts or essential characteristics of the present invention. In this regard, the exemplary embodiments disclosed herein are only for illustrative purposes and should not be construed as limiting the scope of the present invention. On the contrary, the present invention is intended to cover not only the exemplary embodiments but also various alternatives, modifications, equivalents, and other embodiments that may be included within the spirit and scope of the present invention as defined by the appended claims.

INDUSTRIAL APPLICABILITY

The present invention can be used for the detection of apoptosis, screening of anticancer agents or apoptosis-inhibiting materials, inhibition of phagocytosis, protection of apoptosis, and reduction of side-effects that may occur during transplantation.

The invention claimed is:

1. A method for detecting apoptosis, comprising:
   treating a cell-containing sample with a composition comprising a phosphatidylinositol phosphate-binding material labeled with a labeling material;
   binding the phosphatidylinositol phosphate-binding material with the phosphatidylinositol phosphate which is externalized to the surface of the cell if the cell is apoptotic; and
   detecting the labeling material from the sample which is externalized to the surface of the cell,
   wherein the phosphatidylinositol phosphate is phosphatidylinositol-3,4,5-triphosphate (PtdIns(3,4,5)P$_3$) or phosphatidylinositol-4,5-biphosphate (PtdIns(4,5)P$_2$),
   wherein the phosphatidylinositol phosphate-binding material is selected from the group consisting of a protein comprising a pleckstrin homology (PH) domain, a protein comprising the C2 domain of protein kinase C (PKC), an anti-PtdIns(4,5)P$_2$ antibody, an anti-PtdIns(3,4,5)P$_3$ antibody, and a mixture thereof,
   wherein the protein comprising a pleckstrin homology (PH) domain is protein kinase B (Akt).

2. The method of claim 1, wherein the protein comprising the C2 domain is a protein comprising the β1 C2 domain of PKC, to which Myc is bound.

3. The method of claim 1, wherein the apoptosis detection is performed in vitro.

4. The method of claim 1, wherein the labeling material is any one selected from the group consisting of fluorescent materials, chromogenic enzymes, radioisotopes, chromophores, superparamagnetic particles, and ultrasuper paramagnetic particles.

\* \* \* \* \*